US010376323B2

(12) United States Patent
Farritor et al.

(10) Patent No.: US 10,376,323 B2
(45) Date of Patent: Aug. 13, 2019

(54) MULTIFUNCTIONAL OPERATIONAL COMPONENT FOR ROBOTIC DEVICES

(71) Applicant: Board of Regents of the University of Nebraska, Lincoln, NE (US)

(72) Inventors: Shane Farritor, Lincoln, NE (US); Amy Lehman, York, NE (US); Mark Rentschler, Boulder, CO (US); Nathan Wood, Lincoln, NE (US); Jason Dumpert, Omaha, NE (US); Dmitry Oleynikov, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/888,723

(22) Filed: Feb. 5, 2018

(65) Prior Publication Data

US 2018/0153631 A1    Jun. 7, 2018

Related U.S. Application Data

(63) Continuation of application No. 14/936,234, filed on Nov. 9, 2015, now Pat. No. 9,883,911, which is a
(Continued)

(51) Int. Cl.
*A61B 17/00*        (2006.01)
*A61B 34/30*        (2016.01)
(Continued)

(52) U.S. Cl.
CPC ............. *A61B 34/30* (2016.02); *A61B 90/30* (2016.02); *A61B 90/37* (2016.02); *A61B 90/361* (2016.02);
(Continued)

(58) Field of Classification Search
CPC .......... A61B 34/30; A61B 90/30; A61B 90/37
See application file for complete search history.

(56) References Cited

U.S. PATENT DOCUMENTS 3,870,264 A     3/1975   Robinson
3,989,952 A    11/1976   Timberlake et al.
(Continued)

FOREIGN PATENT DOCUMENTS

CN       102821918      12/2012
DE      102010040405     3/2012
(Continued)

OTHER PUBLICATIONS

Abbott et al., "Design of an Endoluminal Notes Robotic System," from the Proceedings of the 2007 IEEE/RSJ Int'l Conf. on Intelligent Robot Systems, San Diego, CA, Oct. 29-Nov. 2, 2007, pp. 410-416.
(Continued)

*Primary Examiner* — John R Downey
(74) *Attorney, Agent, or Firm* — Davis, Brown, Koehn, Shors & Roberts, P.C.; Sean D. Solberg

(57) ABSTRACT

The various embodiments disclosed herein relate to modular medical devices, including various devices with detachable modular components and various devices with pivotally attached modular components. Additional embodiments relate to procedures in which various of the devices are used cooperatively. Certain embodiments of the medical devices are robotic in vivo devices.

20 Claims, 26 Drawing Sheets

Related U.S. Application Data continuation of application No. 14/202,353, filed on Mar. 10, 2014, now Pat. No. 9,179,981, which is a continuation of application No. 12/324,364, filed on Nov. 26, 2008, now Pat. No. 8,679,096, which is a continuation-in-part of application No. 12/192,779, filed on Aug. 15, 2008, now Pat. No. 8,974,440, and a continuation-in-part of application No. 11/766,683, filed on Jun. 21, 2007, now Pat. No. 8,968,332, and a continuation-in-part of application No. 11/966,741, filed on Dec. 28, 2007, now Pat. No. 9,579,088.

(60) Provisional application No. 60/990,086, filed on Nov. 26, 2007, provisional application No. 60/956,032, filed on Aug. 15, 2007, provisional application No. 60/990,076, filed on Nov. 26, 2007, provisional application No. 60/990,106, filed on Nov. 26, 2007, provisional application No. 61/025,346, filed on Feb. 1, 2008, provisional application No. 61/030,617, filed on Feb. 22, 2008, provisional application No. 60/815,741, filed on Jun. 22, 2006, provisional application No. 60/845,608, filed on Sep. 19, 2006, provisional application No. 60/686,030, filed on May 31, 2005, provisional application No. 60/884,792, filed on Jan. 12, 2007, provisional application No. 60/888,182, filed on Feb. 5, 2007, provisional application No. 60/890,691, filed on Feb. 20, 2007, provisional application No. 60/956,032, filed on Aug. 15, 2007, provisional application No. 60/983,445, filed on Oct. 29, 2007.

(51) Int. Cl.
*A61B 90/00* (2016.01)
*A61B 90/30* (2016.01)
*B33Y 80/00* (2015.01)

(52) U.S. Cl.
CPC ..... *A61B 2017/00283* (2013.01); *B33Y 80/00* (2014.12)

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Ortiz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A * | 4/1997 | Smith .............. B25J 3/04 604/95.01 |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A * | 11/1998 | Smith .............. B25J 3/04 604/95.01 |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A * | 9/1999 | Smith .............. B25J 3/04 604/95.01 |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |

(56) References Cited

U.S. PATENT DOCUMENTS

| | | |
|---|---|---|
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |

(56) References Cited

U.S. PATENT DOCUMENTS

| | | |
|---|---|---|
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,353,897 B2 | 1/2013 | Doyle et al. |
| 9,089,353 B2 | 7/2015 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1* | 7/2004 | Saadat .................. A61B 1/0055 600/104 |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1* | 5/2005 | Khalili .................. A61B 1/018 600/106 |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1* | 1/2008 | Farritor .............. A61B 1/00158 606/130 |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1* | 3/2008 | Farritor .............. A61B 1/00158 606/130 |
| 2008/0058989 A1 | 3/2008 | Oleynikov et al. |

(56) References Cited

U.S. PATENT DOCUMENTS

| | | |
|---|---|---|
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1* | 9/2008 | Farritor ............ A61B 17/00234 606/130 |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1* | 2/2009 | Farritor ............ A61B 19/2203 606/130 |
| 2009/0054909 A1* | 2/2009 | Farritor ............ A61B 17/00234 606/130 |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0098529 A1 | 4/2011 | Ostrovsky et al. |
| 2011/0152615 A1* | 6/2011 | Schostek ............ A61B 19/2203 600/111 |
| 2011/0224605 A1 | 9/2011 | Farritor et al. |
| 2011/0230894 A1 | 9/2011 | Simaan et al. |
| 2011/0237890 A1* | 9/2011 | Farritor .................. A61B 34/73 600/142 |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-0162235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |

OTHER PUBLICATIONS

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Green, "Telepresence Surgery", Jan. 1, 1995, Publisher: IEEE Engineering in Medicine and Biology.

Cleary et al., "State of the Art in Surgical Rootics: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

Guber et al., "Miniaturized Instrument Systems for Minimally Invasive Diagnosis and Therapy," Biomedizinische Technic. 2002, Band 47, Erganmngsband 1: 198-201.

Grady, "Doctors Try New Surgery for Gallbladder Removal," The New York Times, Apr. 20, 2007, 3 pp.

Atmel 8005X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

(56) References Cited

OTHER PUBLICATIONS

Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimental Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on in Vivo Sensors for Medicine, Jan. 2007, 10 pp.
Fukuda et al., "Micro Active Catheter System with Multi Degrees of Freedom," Proceedings of the IEEE International Conference on Robotics and Automation, May 1994, pp. 2290-2295.
Fukuda et al., "Mechanism and Swimming Experiment of Micro Mobile Robot in Water," Proceedings of the 1994 IEEE International Conference on Robotics and Automation, 1994: 814-819.
Fraulob et al., "Miniature assistance module for robot-assisted heart surgery," Biomed. Tech. 2002, 47 Suppl. 1, Pt. 1: 12-15.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al, "Tomorrow's surgery: micromotors and microrobots for minimally invasive procedures," Minimally Invasive Surgery & Allied Technologies, 1998; 7(4): 343-352.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6): 1317-1320.

\* cited by examiner

MULTIFUNCTIONAL OPERATIONAL COMPONENT FOR ROBOTIC DEVICES

CROSS-REFERENCE TO RELATED APPLICATION(S)

This application claims priority as a continuation of U.S. application Ser. No. 14/936,234, filed Nov. 9, 2015 and entitled "Multifunctional Operational Component for Robotic Devices," which claims priority as a continuation of U.S. application Ser. No. 14/202,353, filed Mar. 10, 2014 and entitled "Multifunctional Operational Component for Robotic Devices," which issued on Nov. 10, 2015 as U.S. Pat. No. 9,179,981, which claims priority as a continuation of U.S. application Ser. No. 12/324,364, filed Nov. 26, 2008 and entitled "Multifunctional Operational Component for Robotic Devices," which issued on Mar. 25, 2014 as U.S. Pat. No. 8,679,096, which claims priority to U.S. Application 60/990,086, filed Nov. 26, 2007 and entitled "Multifunctional Operational Component," all of which are hereby incorporated herein by reference in their entireties. Additionally, U.S. application Ser. No. 12/324,364 is a continuation-in-part of U.S. application Ser. No. 12/192,779, filed Aug. 15, 2008 and entitled "Modular and Cooperative Medical Devices and Related Systems and Methods," which issued on Mar. 10, 2015 as U.S. Pat. No. 8,974,440, which claims priority to U.S. Application 60/956,032, filed Aug. 15, 2007, U.S. Application 60/990,076, filed Nov. 26, 2007, U.S. Application 60/990,106, filed Nov. 26, 2007, U.S. Application 61/025,346, filed Feb. 1, 2008, and U.S. Application 61/030,617, filed Feb. 22, 2008, all of which are hereby incorporated herein by reference in their entireties. Further, U.S. application Ser. No. 12/324,364 is a continuation-in-part of U.S. application Ser. No. 11/766,683, filed on Jun. 21, 2007 and entitled "Magnetically Coupleable Robotic Devices and Related Methods," which issued on Mar. 3, 2015 as U.S. Pat. No. 8,968,332, which claims priority to U.S. Application 60/815,741, filed Jun. 22, 2006, U.S. Application 60/845,608, filed Sep. 29, 2006, U.S. Application 60/868,030, filed Nov. 30, 2006, U.S. Application 60/884,792, filed Jan. 12, 2007, and U.S. Application 60/888,182, filed Feb. 5, 2007, all of which are hereby incorporated herein by reference in their entireties. In addition, U.S. application Ser. No. 12/324,364 is a continuation-in-part of U.S. application Ser. No. 11/966,741, filed Dec. 28, 2007 and entitled "Methods, Systems, and Devices for Surgical Visualization and Device Manipulation," which claims priority to U.S. Application 60/890,691, filed Feb. 20, 2007, U.S. Application 60/956,032, filed Aug. 15, 2007, and U.S. Application 60/983,445, filed Oct. 29, 2007, all of which are hereby incorporated herein by reference in their entireties.

GOVERNMENT SUPPORT

This invention was made with government support under Grant No. R21EB5663-2, awarded by the National Institute of Biomedical Imaging and Bioengineering within the National Institutes of Health. Accordingly, the government has certain rights in the invention.

FIELD OF THE INVENTION

The embodiments disclosed herein relate to various medical devices and related components, including robotic and/or in vivo medical devices and related components. Certain embodiments include various modular medical devices, including modular in vivo and/or robotic devices. In particular, certain embodiments relate to modular medical devices including various functional and/or multifunctional operational components. Further embodiments relate to methods of operating the above devices, including methods of using various of the devices cooperatively.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional challenges of being very large, very expensive, unavailable in most hospitals, and having limited sensory and mobility capabilities.

BRIEF SUMMARY OF THE INVENTION

One embodiment disclosed herein relates to a modular medical device or system having at least one modular component configured to be disposed inside a cavity of a patient. The modular component has a body, an operational component, and a coupling component. In a further embodiment, the modular component can be coupled at the coupling component to a second modular component. In a further alternative, a third modular component can be coupled to the first and second modular components.

Another embodiment disclosed herein relates to a modular medical device or system having a body configured to be disposed inside a cavity of a patient. The device also has at least a first modular component coupleable to the body, the first modular component having a first operational component. In another embodiment, the device also has a second modular component coupleable to the body, the second modular component having a second operational component. In further alternatives, the device can also have third and fourth modular components or more.

In certain embodiments, the operational component can be a multi-functional operational component. If more than one multi-functional operational component is provided, the multi-functional operational components can be the same as or different from one another. According to one embodiment, a multi-functional operational embodiment includes a first arm having any one of an irrigation component, a suction component, a cautery component, a biopsy component, a sensor component, or a treatment module and a second arm. In some embodiments, the second arm can also include any one of an irrigation component, a suction component, a cautery component, a biopsy component, a sensor component, or a treatment module.

Yet another embodiment disclosed herein relates to a modular medical device or system having a first modular component, a second modular component, and a third modular component. In one embodiment, the three modular components are pivotally connected to each other in a triangular configuration. In this embodiment, the first and third components can be coupled together at a releasable mating connection. According to one embodiment, each of the modular components has an inner body and an outer body, wherein the inner body is rotatable in relation to the outer body. In addition, each modular component has an operational component associated with the inner body. In accordance with another implementation, each of the inner and outer bodies comprise an opening, and each of the inner bodies is rotatable to position the inner and outer openings in communication, whereby the operational components are accessible. In a further alternative, each pivotal connection of the device or system has a mechanism configured to urge the mating or coupling connections at the ends of the first and third components into contact. Alternatively, the device has four modular components that are pivotally connected to each other in a quadrangular configuration. In further alternatives, additional modular components can be pivotally connected to each other.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
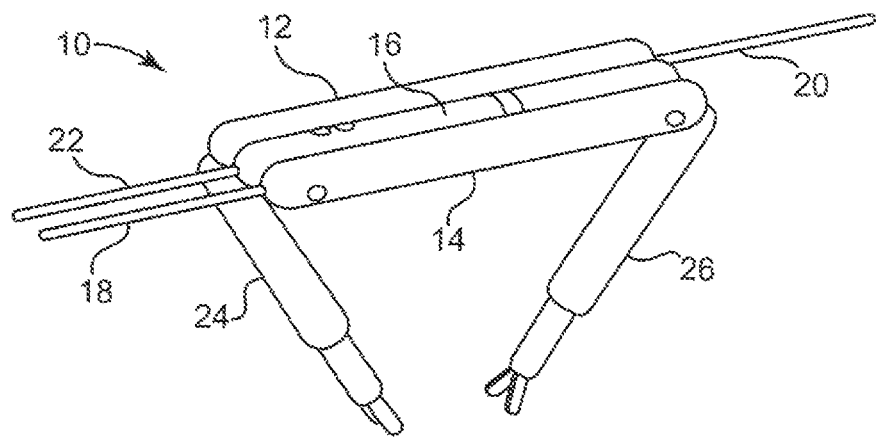
FIG. 1A is a perspective view of a modular medical device, according to one embodiment.

The various systems and devices disclosed herein relate to devices for use in medical procedures and systems. More specifically, various embodiments relate to various modular or combination medical devices, including modular in vivo and robotic devices and related methods and systems, while other embodiments relate to various cooperative medical devices, including cooperative in vivo and robotic devices and related methods and systems.

It is understood that the various embodiments of modular and cooperative devices and related methods and systems disclosed herein can be incorporated into or used with any other known medical devices, systems, and methods.

For example, the various embodiments disclosed herein can be incorporated into or used with any of the medical devices and systems disclosed in copending U.S. applications Ser. No. 11/932,441 (filed on Oct. 31, 2007, and entitled "Robot for Surgical Applications"), Ser. No. 11/695,944 (filed on Apr. 3, 2007, and entitled "Robot for Surgical Applications"), Ser. No. 11/947,097 (filed on Nov. 27, 2007, and entitled "Robotic Devices with Agent Delivery Components and Related Methods), Ser. No. 11/932,516 (filed on Oct. 31, 2007, and entitled "Robot for Surgical Applications"), Ser. No. 11/766,683 (filed on Jun. 21, 2007, and entitled "Magnetically Coupleable Robotic Devices and Related Methods"), Ser. No. 11/766,720 (filed on Jun. 21, 2007, and entitled "Magnetically Coupleable Surgical Robotic Devices and Related Methods"), Ser. No. 11/966,741 (filed on Dec. 28, 2007, and entitled "Methods, Systems, and Devices for Surgical Visualization and Device Manipulation"), Ser. No. 12/171,413 (filed on Jul. 11, 2008, and entitled "Methods and Systems of Actuation in Robotic Devices"), 60/956,032 (filed on Aug. 15, 2007), 60/983,445 (filed on Oct. 29, 2007), 60/990,062 (filed on Nov. 26, 2007), 60/990,076 (filed on Nov. 26, 2007), 60/990,086 (filed on Nov. 26, 2007), 60/990,106 (filed on Nov. 26, 2007), 60/990,470 (filed on Nov. 27, 2007), 61/025,346 (filed on Feb. 1, 2008), 61/030,588 (filed on Feb. 22, 2008), and 61/030,617 (filed on Feb. 22, 2008), all of which are hereby incorporated herein by reference in their entireties.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations disclosed herein relate to modular medical devices that can be assembled in a variety of configurations.

Figure 1B:
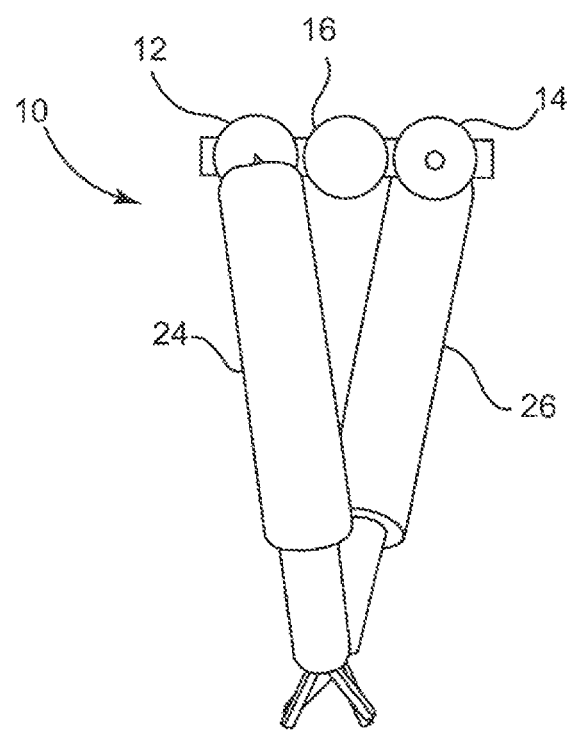
FIG. 1B is a side view of the modular medical device of FIG. 1A.
Figure 1C:
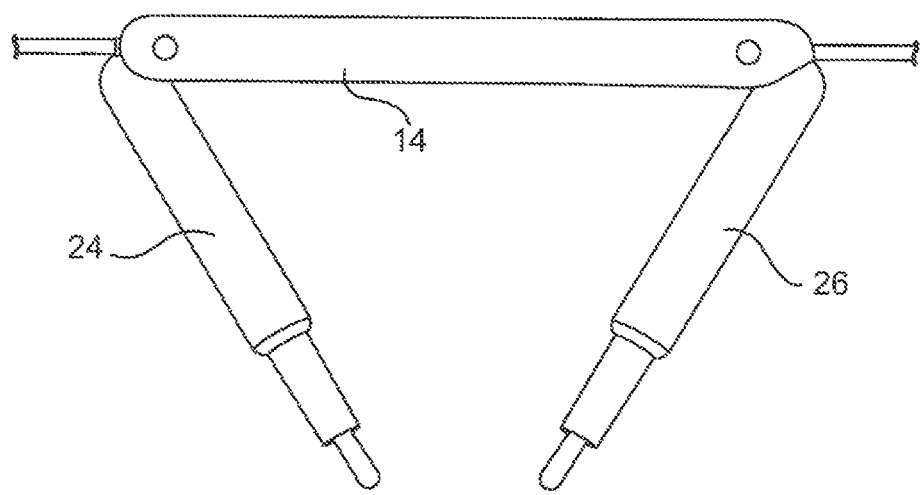
FIG. 1C is a front view of the modular medical device of FIG. 1A.

FIGS. 1A-1C depict an exemplary "combination" or "modular" medical device 10, according to one embodiment. For purposes of this application, both "combination device" and "modular device" shall mean any medical device having modular or interchangeable components that can be arranged in a variety of different configurations. The combination device 10 shown in FIGS. 1A-1C has three modular components 12, 14, 16 coupled or attached to each other. More specifically, the device 10 has two robotic arm modular components 12, 14 and one robotic camera modular component 16 disposed between the other two components 12, 14. In this implementation, the modular component 16 contains an imaging component (not shown) and one or more lighting components (not shown), while each of the other modular components 12, 14 have an arm 24, 26 respectively and do not contain any lighting or imaging components. That is, in this embodiment, the modular component 16 is a modular imaging and lighting component 16 while the two modular components 12, 14 are modular arm components 12, 14. In the resulting configuration, the components 12, 14, 16 are coupled or attached to each such that the camera component 16 is disposed between the two modular arm components 12, 14. As will be discussed in further detail below, this configuration of the components 12, 14, 16 is merely one of several possible configurations of such modular components.

In accordance with one embodiment, the strategic positioning of various operational components in the combination device 10 in FIGS. 1A-1C results in an optimization of the volume in each of the individual components 12, 14, 16. That is, the space in modular components 12, 14 that would have been required for an imaging component and/or a lighting component is instead utilized for larger and/or more complex actuators or other components. If larger or more complex actuators are utilized in both modular components 12, 14, greater force can be applied to each arm 24, 26, thereby making it possible for the combination device 10 to perform additional procedures that require greater force.

In comparison to the space optimization advantage of the combination device 10, a non-combination device must have all the necessary components such as imaging and illumination components in the device body along with the actuators, thereby reducing the space available and requiring that the actuators and other components be small enough such that they all fit in the device together.

According to one alternative embodiment, the additional space available in the combination device 10 created by the space optimization described above could be used to provide for more sophisticated components such as more complex camera focusing mechanisms or mechanisms to provide zoom capabilities. In a further alternative, the various components could be distributed across the modular components 12, 14, 16 of the combination device 10 in any fashion. For example, the illumination and imaging components could be both positioned in either modular component 12 or 14. Alternatively, one of the illumination and imaging components could be disposed in any one of the three modular components 12, 14, 16 and the other component could be disposed in one of the other three components 12, 14, 16. It is understood that any possible combination of various components such as illumination, actuation, imaging, and any other known components for a medical device can be distributed in any combination across the modular components of any combination device.

Another advantage of the combination devices such as that shown in FIGS. 1A-1C, according to one implementation, is the capacity to increase the number of a particular type of component in the device. For example, one embodiment of a combination device similar to the device 10 in FIGS. 1A-1C could have lighting components on more than one of the modular components 12, 14, 16, and further could have more than one lighting component on any given modular component. Thus, the combination device could have a number of lighting components ranging from one to any number of lighting components that could reasonably be included on the device. The same is true for any other component that can be included in two or more of the modular components.

In accordance with a further embodiment, another possible advantage of the various combination device embodiments disclosed herein relates to the fact that the various separable modular components (instead of one larger device) simplifies insertion because each component separately is shorter and less complex. Thus, each component individually has a smaller cross-section and can be inserted into a body cavity through a smaller incision, port, or any other known delivery device than the larger, non-combination device.

It is understood that, according to various embodiments, a combination device such as the device 10 depicted in FIGS. 1A-1C could have additional modular components coupled thereto. Thus, the device could have additional arms or other modular components such as, for example, one or more of a sensing modular component, an illumination modular component, and/or a suction/irrigation modular component.

In use, modular components (such as, for example, components 12, 14, 16 of FIGS. 1A, 1B, and 1C) are each separately inserted into the target cavity of a patient. Typically, each of the components are inserted through a laparoscopic port, an incision, or a natural orifice. Alternatively, the components are inserted by any known method, procedure, or device. Once each of the desired components (which could range from one to several components) is positioned in the target cavity, the components can be assembled into a combination device such as, for example, the combination device 10 depicted in FIGS. 1A-1C, by coupling the components together in a desired configuration. After the procedure has been performed, the components of the combination device can be decoupled and each separately removed. Alternatively, once a portion of a procedure is performed, one or more of the components can be decoupled and removed from the cavity and one or more additional components can be inserted into the cavity and coupled to the combination device for one or more additional procedures for which the component replacement was necessary.

The various modular component embodiments disclosed herein can be coupled to create a combination device in a variety of ways. To configure the combination device 10 as shown in FIG. 1A, the exemplary modular components 12, 14, 16 each have four mating or coupling components as best shown in FIGS. 2A, 2B, and 3.

Figure 2A:
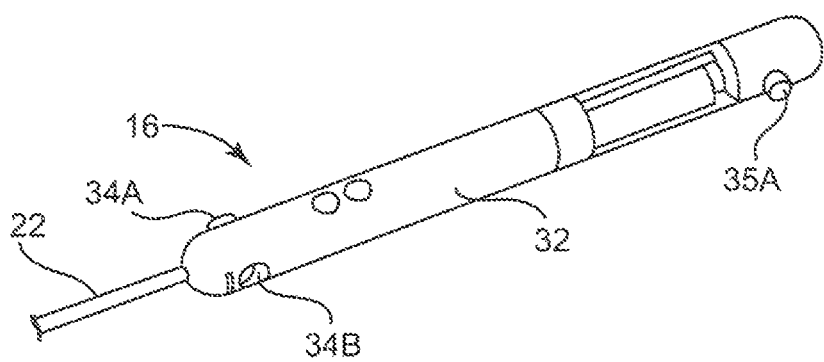
FIG. 2A depicts a perspective view of a modular component, according to one embodiment.
Figure 2B:
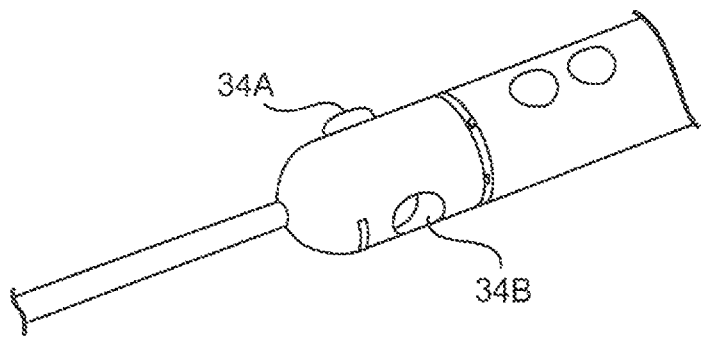
FIG. 2B depicts a close-up perspective view of a portion of the modular component of FIG. 2A.
Figure 3:
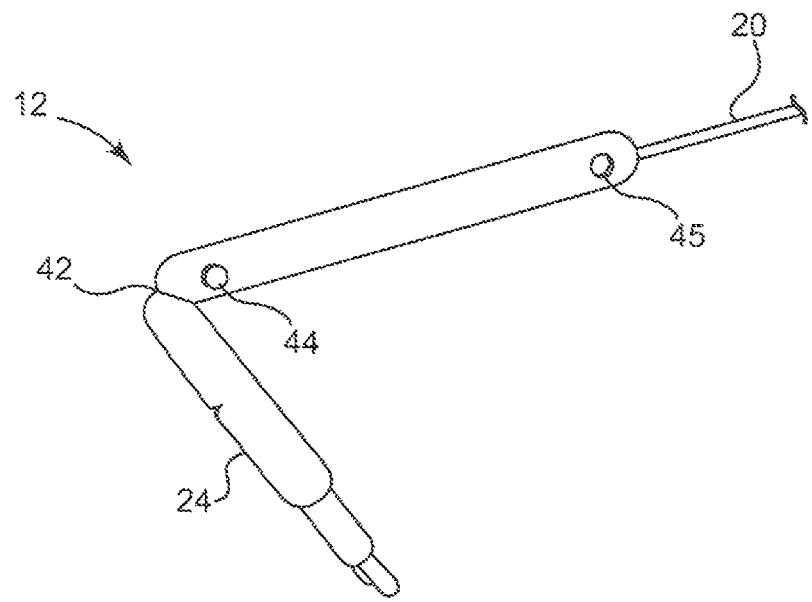
FIG. 3 is a perspective view of another modular component, according to another embodiment.

In FIGS. 2A and 2B, the modular component 16 provides one example of an attachment mechanism for coupling modular components together. That is, the device 16 has four mating or coupling components 34A, 34B, 35A, (and 35B, which is not shown) for coupling to other devices or modular components. In this embodiment as best shown in FIG. 2A, there are two coupling components 34, 35 at each end of the device 30, with two components 34A, 34B at one end and two more at the other end (depicted as 35A and another such component on the opposite side of the component 16 that is not visible in the figure). Alternatively, the modular component 16 can have one coupling component, two coupling components, or more than two coupling components.

To better understand the coupling components of this embodiment, FIG. 2B provides an enlarged view of one end of the device 16, depicting the male coupling component 34A and female coupling component 34B. The male component 34A in this embodiment is configured to be coupleable with a corresponding female component on any corresponding modular component, while the female component 34B is configured to be coupleable with a corresponding male component on any corresponding modular component.

It is understood that the mechanical male/female coupling components discussed above are merely exemplary coupling mechanisms. Alternatively, the components can be any known mechanical coupling components. In a further alternative, the coupling components can also be magnets that can magnetically couple with other magnetic coupling components in other modular components. In a further embodiment, the coupling components can be a combination of magnets to help with initial positioning and mechanical coupling components to more permanently couple the two modules.

Returning to the embodiment depicted in FIG. 1A, two modular components 12, 14, each having an arm 24, 26 (respectively), are coupled to the modular component 16. FIG. 3 depicts component 12, but it is understood that the following discussion relating to modular component 12 applies equally to component 14. Modular component 12 as shown in FIG. 3 has male/female coupling components 44, 45 that can be coupled to component 16 as discussed above. Alternatively, as discussed above, any known coupling components can be incorporated into this component 12 for coupling with other modular components.

According to one implementation, the arm 24 in the embodiment of FIG. 3 provides the four degrees of freedom ("DOF"). These four degrees of freedom include three rotations and one extension. Two rotations occur about the joint 42. The third rotation occurs along the axis of the arm 24. The extension also occurs along the axis of the arm 24. Alternatively, any known arm implementation for use in a medical device can be used.

Figure 4:
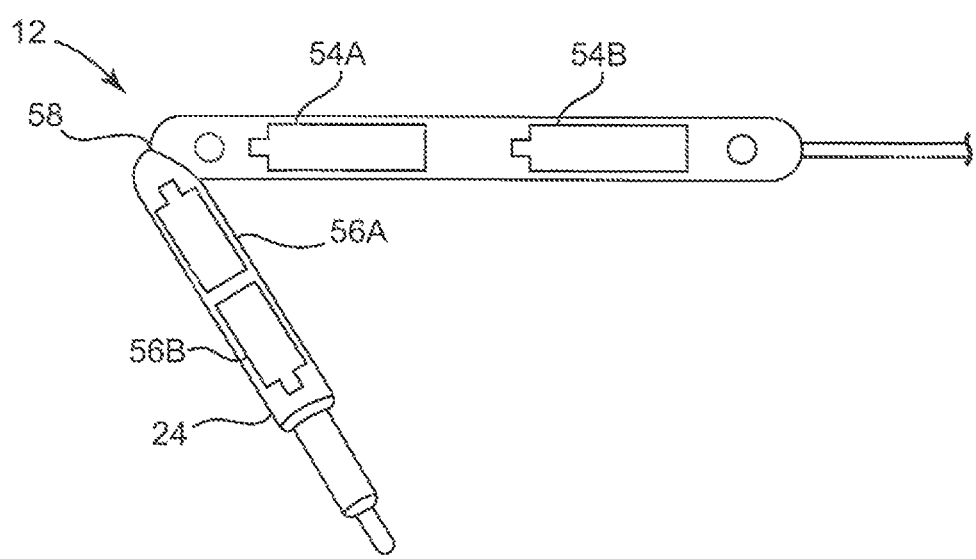
FIG. 4 is a front cutaway view of another modular component, according to a further embodiment.

FIG. 4 depicts an alternative exemplary embodiment of modular component 12. In this implementation, the actuator components 54A, 54B, 56A, 56B are depicted in the component 12. That is, two actuators 54A, 54B are provided in the body of the device 12, while two additional actuators 56A, 56B are provided in the arm 24. According to one embodiment, actuators 54A, 54B are configured to actuate movement of the arm 24 at the shoulder joint 58, while actuators 56A, 56B are configured to actuate movement at the arm 24. Alternatively, it is understood that any configuration of one or more actuators can be incorporated into a modular component to actuate one or more portions of the component or device.

In accordance with further implementations, it is understood that the various modular components discussed herein can contain any known operational components contained in any non-modular medical device. For example, the modular component 16 has a camera 32 and further can have all of the associated components and/or features of the modular components or medical devices discussed above, including the medical devices and components disclosed in the applications incorporated above.

In the depicted embodiment, the modular component 16 has a connection component or "cable" 22 that can be connected at the other end of the cable 22 to a controller (not shown). Similarly, each of modular components 12, 14 also can have a connection component (18, 20 respectively). In alternative implementations, the combination device 10 could have a single cable connected to one of the modular components. In such implementations, the coupling components also provide for communication connections among the modular components such that power, control signals or commands, video, and any other form of communication can be transported or communicated among the modular components.

Figure 5A:
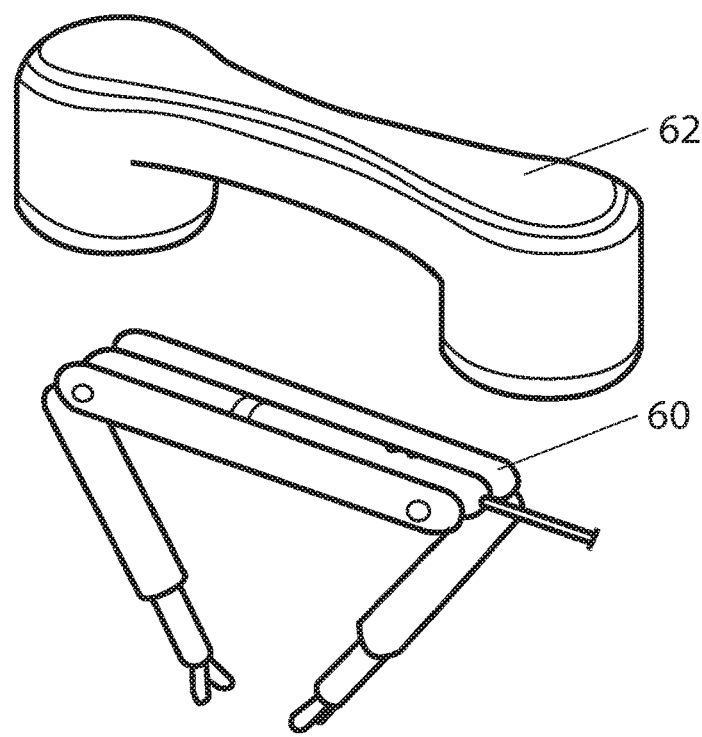
FIG. 5A is a perspective view of a modular medical device control system, according to one embodiment.
Figure 5B:
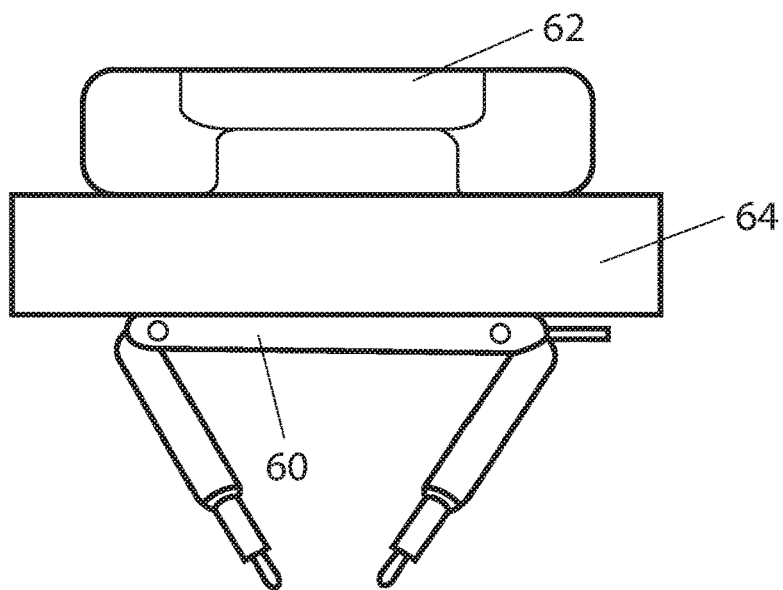
FIG. 5B is a front cutaway view of the system of FIG. 5A.

In use, the various modular components and combination devices disclosed herein can be utilized with any known medical device control and/or visualization systems, including those systems disclosed in the applications incorporated above. These modular components and combination devices can be utilized and operated in a fashion similar to any medical devices disclosed in those applications. For example, as shown in FIGS. 5A and 5B, a combination device or modular component 60 can be utilized with an external magnetic controller 62. In this embodiment, the device 60 has magnetic components (not shown) that allow the device 60 to be in magnetic communication with the external controller 62. It is understood that the device 60 can operate in conjunction with the external controller 62 in the same fashion described in the applications incorporated above.

In an alternative use, any of the individual modular components can operate as an independent device as well. That is, it is understood that any individual component can be inserted into a body cavity and operated without coupling it to any other modular components. As such, each modular component can also be considered a separate device.

Figure 6A:
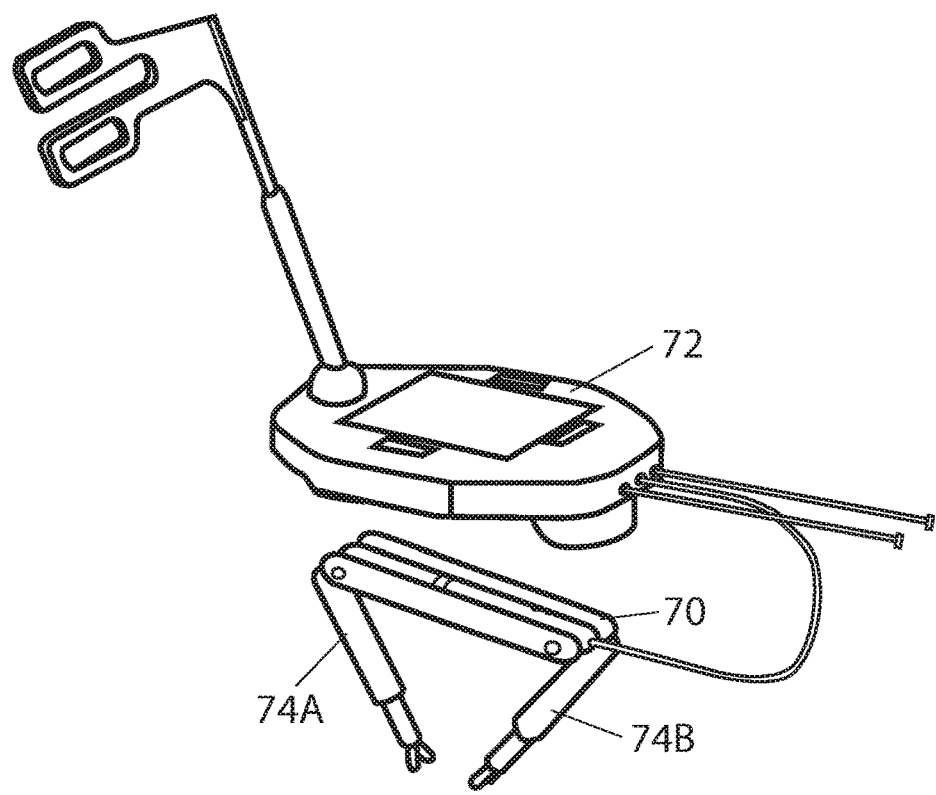
FIG. 6A is a perspective view of a modular medical device control and visualization system, according to one embodiment.
Figure 6B:
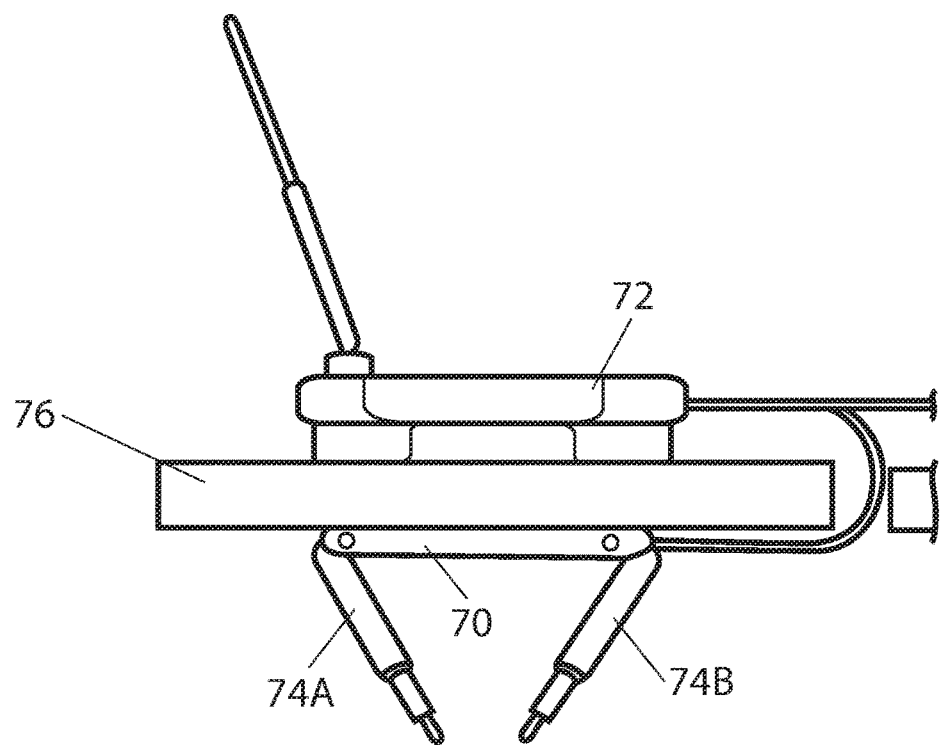
FIG. 6B is a front cutaway view of the system of FIG. 6A.

In another similar example as depicted in FIGS. 6A and 6B, a combination device or modular component 70 can be utilized with an external controller and visualization component 72. In this embodiment, the device 70 has magnetic components (not shown) that allow the device 70 to be in magnetic communication with the external controller 72 and further has arms 74A, 74B that can be operated using the controller 72. It is understood that the device 70 can operate in conjunction with the external component 72 in the same fashion described in the applications incorporated above.

Figure 7A:
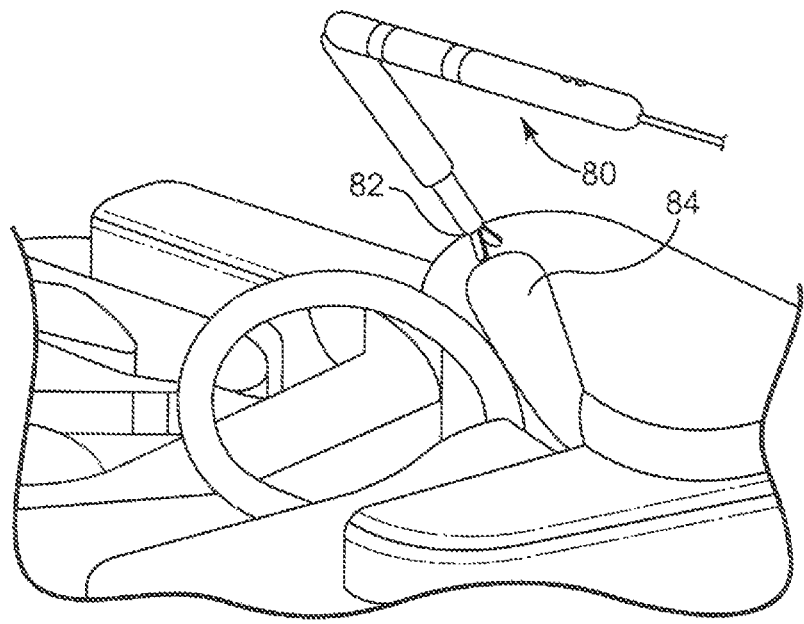
FIG. 7A is a perspective cutaway view of a modular medical device control and visualization system, according to another embodiment.
Figure 7B:
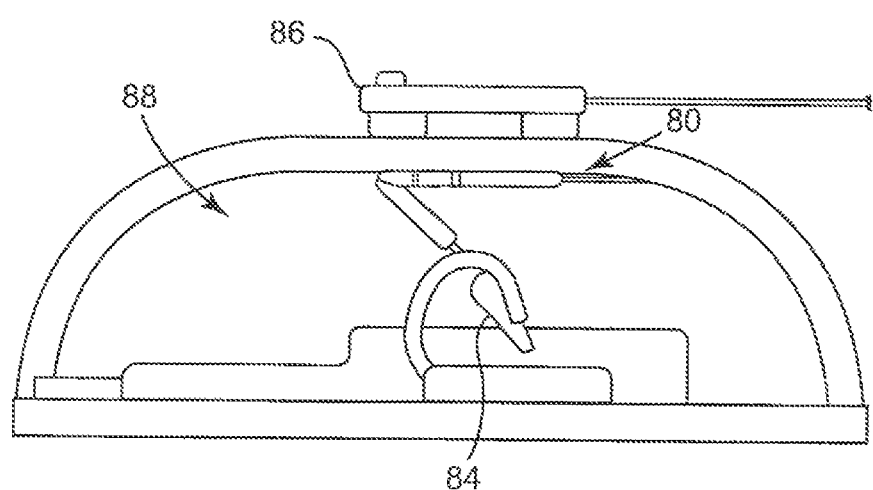
FIG. 7B is a front cutaway view of the system of FIG. 7A.

According to one implementation, a modular device can be used for a variety of surgical procedures and tasks including, but not limited to, tissue biopsy and tissue retraction. For example, as shown in FIGS. 7A and 7B in accordance with one embodiment, a device 80 having a grasper 82 can be used to retract the gall bladder 84 during a cholecystectomy procedure.

Figure 8A:
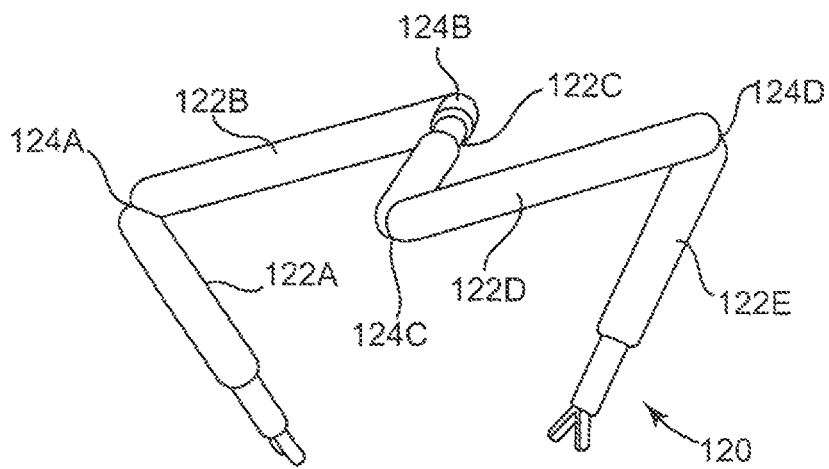
FIG. 8A is a perspective view of a modular medical device, according to another embodiment.
Figure 8B:
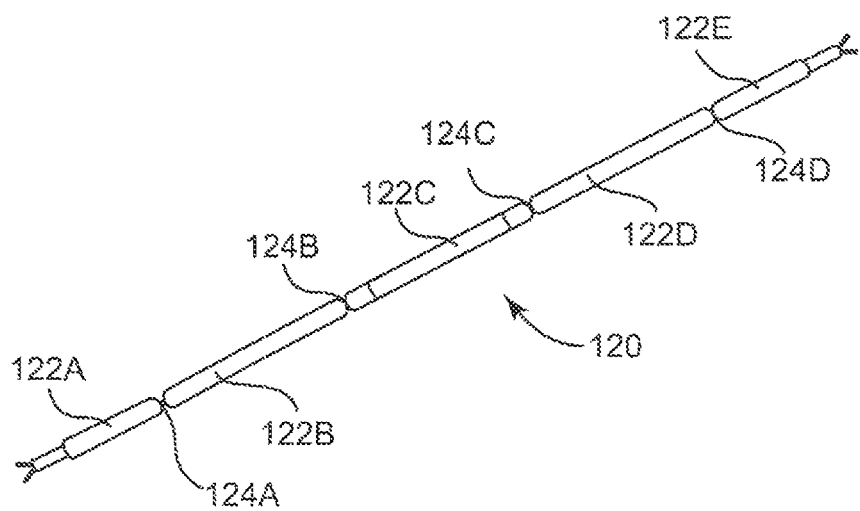
FIG. 8B is another perspective view of the device of FIG. 8A.

In accordance with one alternative, any of the modular components disclosed herein can be assembled into the combination device prior to insertion into the patient's cavity. One exemplary embodiment of such a combination device is set forth in FIGS. 8A and 8B, which depict a combination device 120 having modular components 122A, 122B, 122C, 122D, 122E that are coupled to each other using hinge or rotational joints 124A, 124B, 124C, 124D, 124E (as best shown in FIG. 8B). This device 120 as shown can fold together or otherwise be configured after insertion as shown in FIG. 8A. One advantage of this embodiment, in which the modular components 122A-122E are coupled to each other, is that in vivo assembly of the combination device 120 is simplified.

Figure 9:
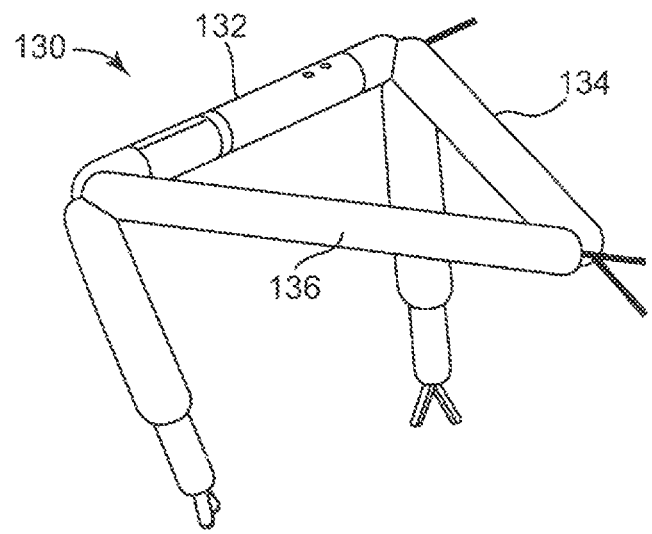
FIG. 9 is a perspective view of another modular medical device, according to a further embodiment.

In a further alternative embodiment as best shown in FIG. 9, any of the modular components disclosed or contemplated herein are inserted separately into the target cavity and subsequently assembled with the modular components being connected end-to-end (in contrast to a side-by-side configuration similar to that depicted in FIGS. 1A-1C). More specifically, the combination device 130 in FIG. 9 has three modular components 132, 134, 136. One of the components is a camera modular component 132, while the other two are robotic arm modular components 134, 136. These three components 132, 134, 136 are connected to form the tripod-like combination device 130 as shown.

Figure 10:
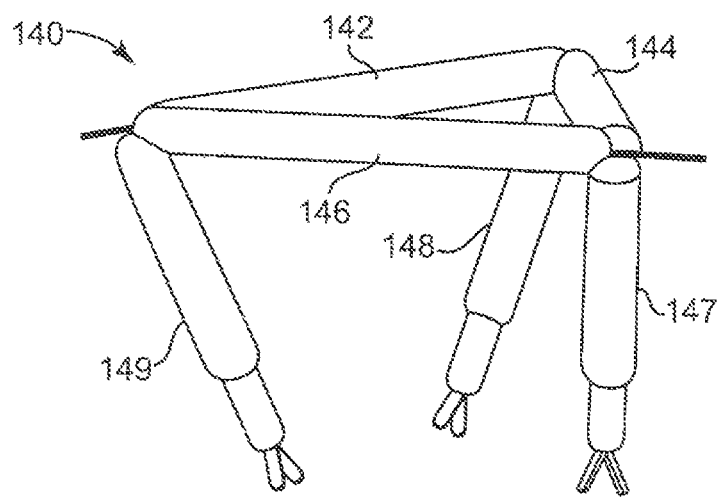
FIG. 10 is a perspective view of a further modular medical device, according to another embodiment.

In yet another implementation, FIG. 10 depicts another combination device 140 having a generally triangular configuration. That is, the device 140 has three arm modular components 142, 144, 146 that are coupled together end-to-end, with each component 142, 144, 146 having an arm 148, 147, 149, respectively. In one embodiment, the three-armed robot could be assembled using three one-arm segments as shown in FIG. 10. Alternatively, the three-armed robot could be assembled by linking three modular bodies end-to-end and coupling an arm component to each linkage of the modular bodies.

Alternatively, additional modular components could be added to a tripod-like combination device such as the devices of FIGS. 9 and 10. For example, one or more additional modular components could be positioned adjacent and parallel to one or more of the three previously-coupled modular components such that one or more sides of the three sides have a "stacked" configuration with at least two modular components stacked next to each other.

As mentioned above, according to one embodiment, a particularly useful aspect of using modular medical devices during medical procedures, including modular robotic and/or in vivo devices as described herein, is the ability to insert multiple modular components, such as any of the modular components described or contemplated herein, into a patient's body and subsequently assemble these into a more complex combination device in vivo. In one implementation, more than one modular component is inserted or positioned in the patient's body (through a natural orifice or more conventional methods) and then the components are either surgically assembled or self-assembled once inside the patient's body, in a location such as the peritoneal cavity, for example.

Surgical (or procedural) assembly can involve the surgeon attaching the modular components by using standard laparoscopic or endoscopic tools, or could involve the surgeon using specifically developed tools for this purpose. Alternatively, surgical assembly could instead or further include the surgeon controlling a robotic device disposed within the patient's body or exterior to the body to assemble the modular components. Self assembly, on the other hand, can involve the modular components identifying each other and autonomously assembling themselves. For example, in one embodiment of self assembly, the modular components have infrared transmitters and receivers that allow each component to locate attachment points on other components. In another example, each modular component has a system that utilizes imaging to identify patterns on other modular components to locate attachment points on those other components. In a further alternative, assembly could also include both surgical and self-assembly capabilities.

After the surgical procedure is completed, the components are disassembled and retracted. Alternatively, the robotic device or system can be configurable or reconfigurable in vivo to provide different surgical features during different portions of the procedure. That is, for example, the components of the device or devices can be coupled together in one configuration for one procedure and then disassembled and re-coupled in another configuration for another procedure.

One further exemplary embodiment of a suite of modular components is set forth in FIGS. 11-17. It is understood that such a suite of components can be made available to a surgeon or user, and the surgeon or user can utilize those components she or he desires or needs to create the combination device desired to perform a particular procedure. In one embodiment, since the devices and components are modular, the user (or team) can assemble the procedure-specific robotic device or devices in vivo at the onset of the procedure.

The modular components can include any known procedural or operational component, including any component discussed elsewhere herein (such as those depicted in FIGS. 1A-4, and/or 8A-10) or any component disclosed in the applications incorporated above that can be used as modular component. For example, the various modular components depicted in FIGS. 11-17 include a variety of different operational components or other types of components, as will be described in further detail below.

Figure 11:
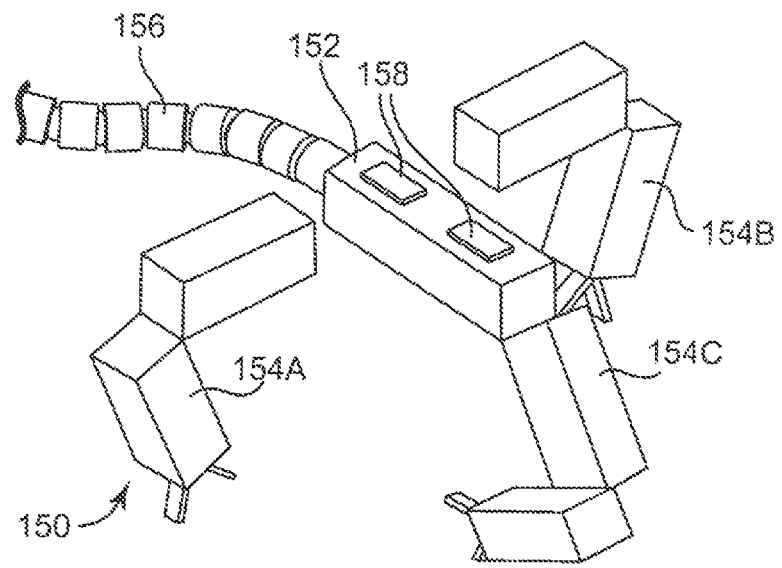
FIG. 11 is a perspective view of another modular medical device, according to one embodiment.
Figure 12A:
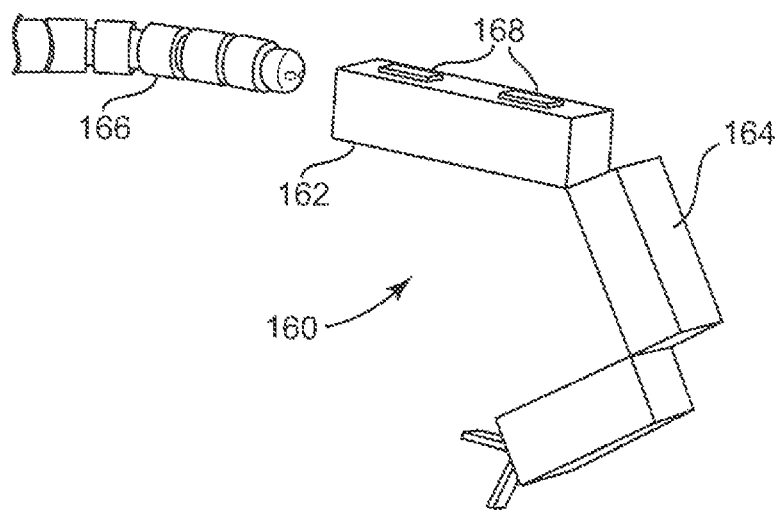
FIG. 12A is a perspective view of another modular medical device, according to a further embodiment.
Figure 12B:
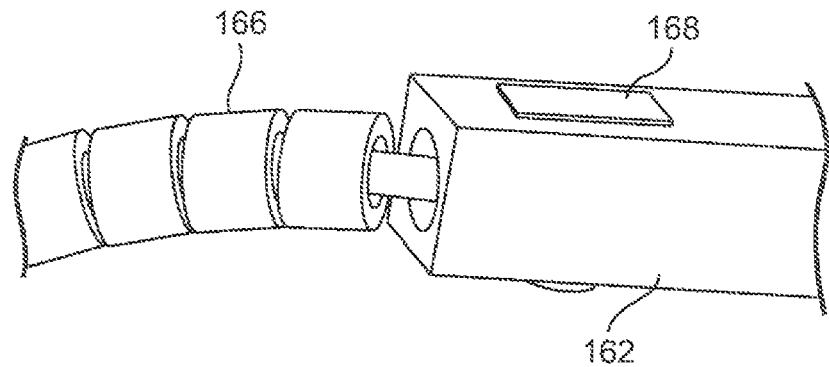
FIG. 12B is a close-up perspective view of a part of the device of FIG. 12A.
Figure 12C:
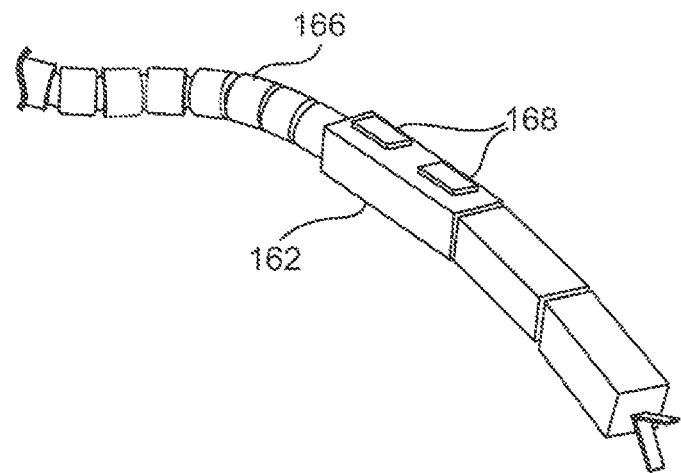
FIG. 12C is another perspective view of the device of FIG. 12A.
Figure 13:
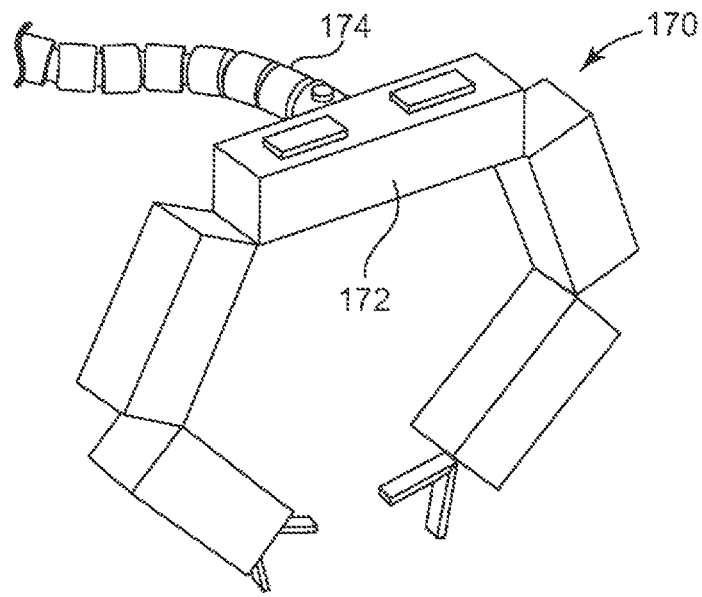
FIG. 13 is a perspective view of a further modular medical device, according to another embodiment.

More specifically, FIGS. 11-13 depict various modular combination device embodiments having a body that is coupled to at least one arm component and a lockable tube. For example, FIG. 11 shows a combination device 150 having a body 152 coupled to three operational arm components 154A, 154B, 154C, and a lockable tube 156. In one aspect, the body 152 can also have at least one magnet 158 (or two magnets as depicted in the figure) that can be used to position the device within the patient's cavity. That is, according to one implementation similar to those described above in relation to other devices, the magnet(s) 158 can be magnetically coupled to an external magnet controller or visualization component to position the device 150.

The lockable tube 156 can be a reversibly lockable tube as disclosed in U.S. application Ser. No. 12/171,413, filed on Jul. 11, 2008, which is incorporated by reference above. The tube 156 and device 150 can be operated in any fashion as described in that application. Alternatively, the tube 156 can be a flexible tube that can be stabilized or held in place using a series of magnets adjacent to or near the flexible tube or a series of needles inserted through the external wall of the patient's body. For example, magnets can be positioned in one or more of the modular components of the flexible tube. In use, one or more magnets are positioned externally with respect to the target cavity in such a fashion as to position the tube and/or robotic device into the desired location.

In use, as also described in the above-incorporated application, a reversibly lockable tube and robotic device (such as, for example, the tube 156 and device 150 depicted in FIG. 11) can be used together to accomplish various tasks. That is, the tube can be operably coupled to the device (as shown in FIG. 11, for example) and contain any required connection components such as connections for hydraulic, pneumatic, drive train, electrical, fiber optic, suction, or irrigation systems, or any other systems or connections that require physical linkages between the device positioned in the patient's body and some external component or device. In one embodiment, the robotic device is first positioned at the desired location in the patient's body and then the tube is inserted and connected to the device. Alternatively, the robotic device can be coupled to the tube prior to insertion, and then both the device and the tube are inserted into the patient's body and the device is then positioned at the desired location.

FIGS. 12A-12C depict another embodiment of a combination device coupled to a lockable tube. More specifically, FIGS. 12A, 12B, and 12C depict a combination device 160 having a body 162 coupled to one operational arm component 164 and a lockable tube 166. As with the device in FIG. 11, the body 162 has two magnets 168 that can be used in conjunction with an external magnet controller to position the device 160 and tube 166 as desired by the user. Alternatively, the body 162 can have one magnet or more than two magnets. In addition, according to one embodiment as best shown in FIG. 12A, the device 160 and the tube 166 can be initially unattached. Prior to use, the body 162 and tube 166 can be coupled as best shown in FIG. 12B. In one embodiment, the body 162 and tube 166 can be coupled prior to insertion or alternatively can be coupled after the device 160 and tube 166 have been positioned in the desired location in the patient's body.

FIG. 13 shows another embodiment of another combination device 170 similar to those depicted in FIGS. 11-12C except that the body 172 is coupled to the tube 174 at a location along the body 172 rather than at an end of the body 172. It is further understood that a tube as disclosed herein can be coupled to any of these combination devices at any point along the body or any of the modular components.

Figure 14:
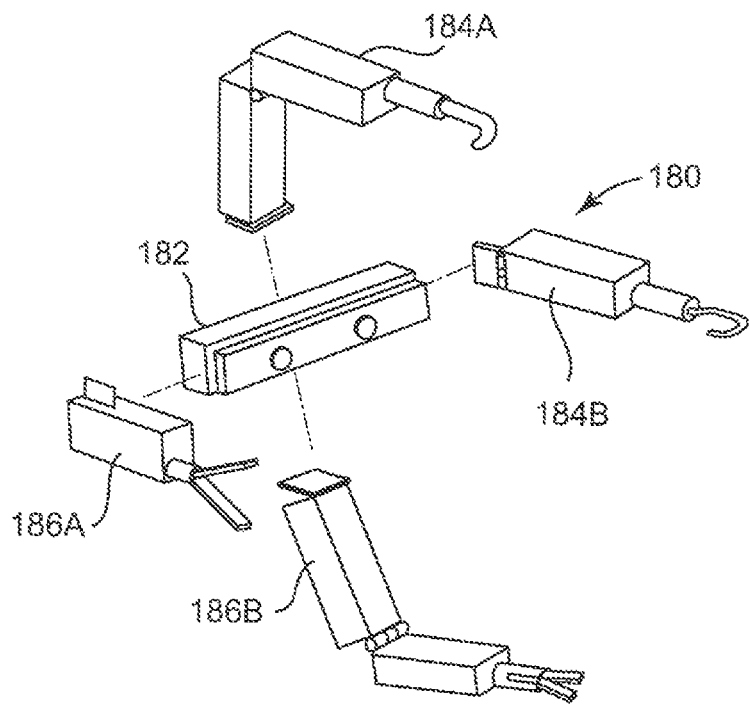
FIG. 14 is a perspective view of the disassembled components of another modular medical device, according to one embodiment.

Another example of a combination device that is made up of a suite of modular components is set forth in FIG. 14. The combination device 180 has an imaging modular component 182 (also referred to as a "module"), two cautery arms or modules 184A, 184B, and two grasper arms or modules 186A, 186B. It is understood that the imaging module 182 in this embodiment is the body 182 of the device 180, but could also be an arm in another implementation. It is further understood that the various modules 184, 186 coupled to the device 180 could be configured in any configuration.

Figure 15:
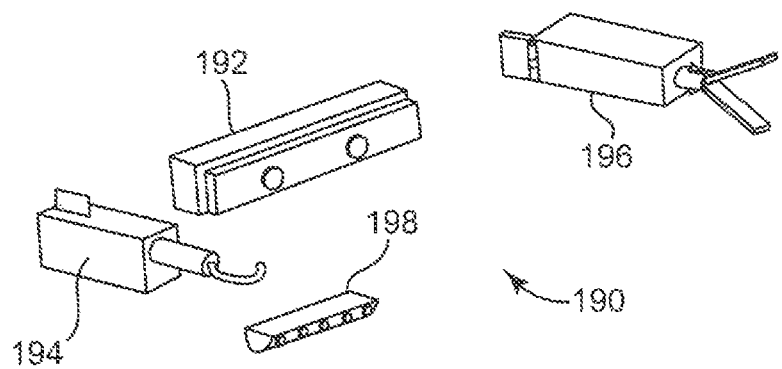
FIG. 15 is a perspective view of the disassembled components of a further modular medical device, according to another embodiment.
Figure 16:
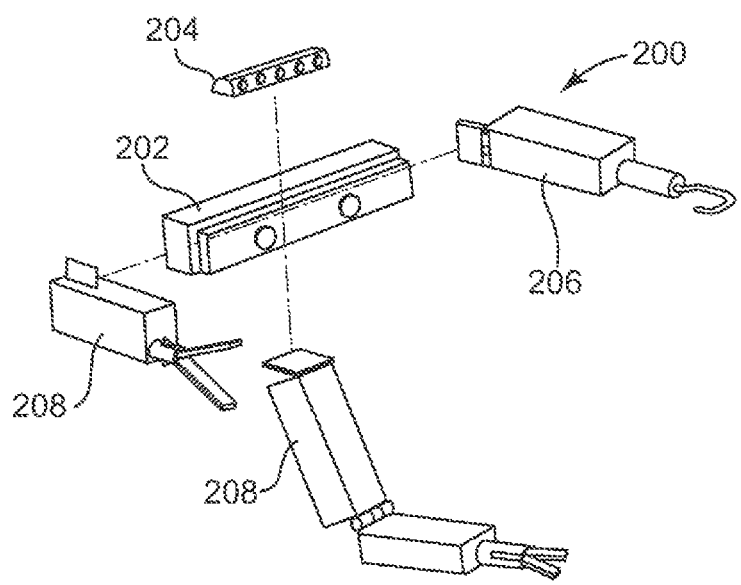
FIG. 16 is a perspective view of the disassembled components of a further modular medical device, according to another embodiment.

An alternative combination device embodiment utilizing various modules from a suite of modular components is depicted in FIG. 15. This device 190 has an imaging module 192, a cautery module 194, a grasper module 196, and a lighting module 198. Similarly, FIG. 16 depicts yet another alternative combination device 200 having an imaging module 202, a lighting module 204, a cautery module 206, and two grasper modules 208.

Figure 17:
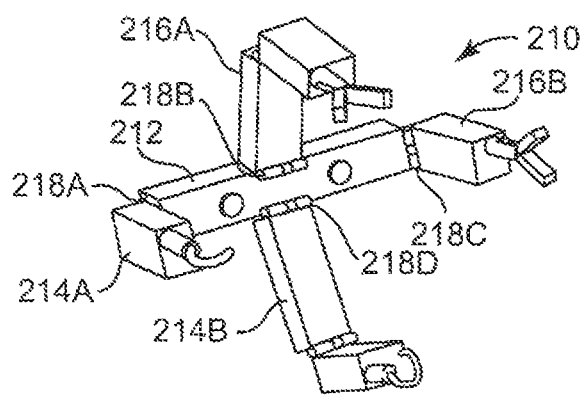
FIG. 17 is a perspective view of an assembled modular medical device, according to a further embodiment.

FIG. 17 depicts a further alternative implementation of a fully assembled combination device 210 having a body 212, two cautery modules 214A, 214B, and two grasper modules 216A, 216B. As shown in the figure, each of the modules is coupled to the body via a hinge coupling 218A, 218B, 218C, 218D. Alternatively, the coupling can be any known coupling, including, for example, a pivotal coupling. In a further alternative, the non-arm modules can be substantially or removably fixed to the body component, such as the lighting module 204 depicted in FIG. 16.

It is understood that any number of additional exemplary modular components could be included in the suite of modular components available for use with these devices. For example, various additional exemplary modules include, but are not limited to, an imaging module, a sensor module (including a pH, humidity, temperature, and/or pressure sensor), a stapler module, a UV light module, an X-ray module, a biopsy module, or a tissue collection module. It is understood that "module" is intended to encompass any modular component, including an arm or a body as discussed above.

Various modules including a variety of exemplary operational components will now be described. An operational component, as described herein, is generally associated with a robotic device, and may have one or more subcomponents or functionalities. An operational component may also be referred to as an "end effector." It is generally understood that any one of the exemplary operational components and modules described below can be included in a suite of modular components used to form the robotic devices as described herein according to the various embodiments. In a further embodiment, any of the operational components described herein can be used in conjunction with any non-modular versions of these devices or systems. Additionally, the exemplary operational components and modules can be used with other surgical robotic devices as are known to those of skill in the art.

Figure 18A:
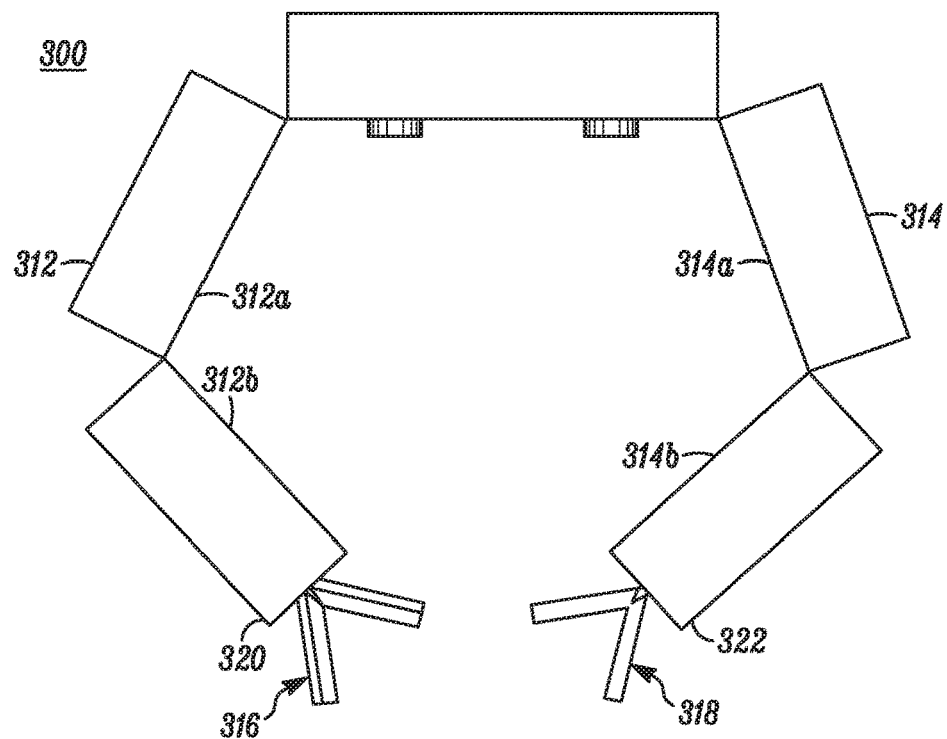
FIG. 18A is a close-up, schematic view of an operational component according to one embodiment.
Figure 18B:
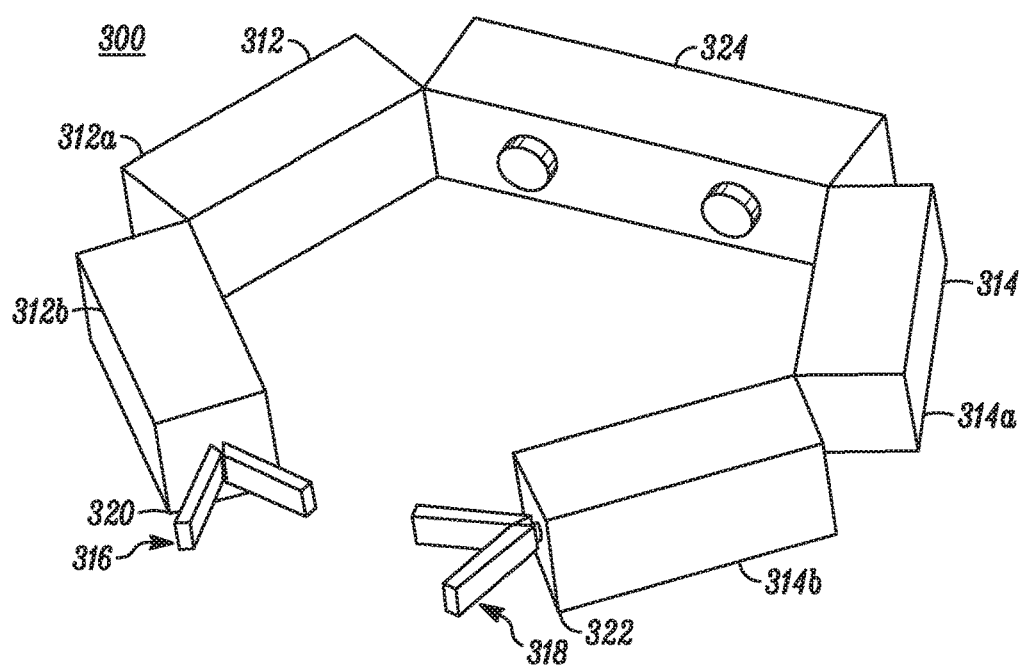
FIG. 18B is a schematic view of a robotic device including the operational component shown in FIG. 18A.

FIGS. 18A and 18B depict a robotic device 300 according to one embodiment. As shown in FIGS. 18A and 18B the device 300 has two arms 312, 314 each having a first link 312a, 314a and a second link 312b, 314b. Each arm 312, 314 also includes operational components 316, 318 operably coupled at distal end 320, 322 of each arm 312, 314. The operational components 316, 318 can be the same or different from one another. In one embodiment, at least one of operational components 316, 318 is a multi-functional operational component as described herein. In another embodiment, both of the operational components 316, 318 are multifunctional operational components as described herein. "Multi-functional operational components" are operational components capable of performing more than one function.

In some embodiments, the robotic device 300 can also include a body 324 that is a viewing module having appropriate lighting and/or a camera to assist in viewing the procedure. As shown in FIGS. 18A and 18B, the body 324 is disposed between and is coupled to the two arms 312, 314.

Figure 19A:
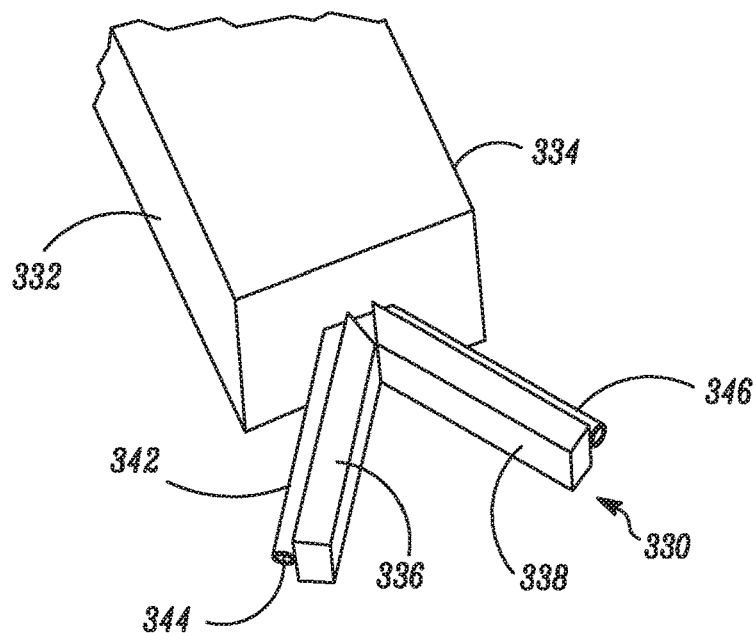
FIG. 19A is a close-up, schematic view of an operational component according to one embodiment.
Figure 19B:
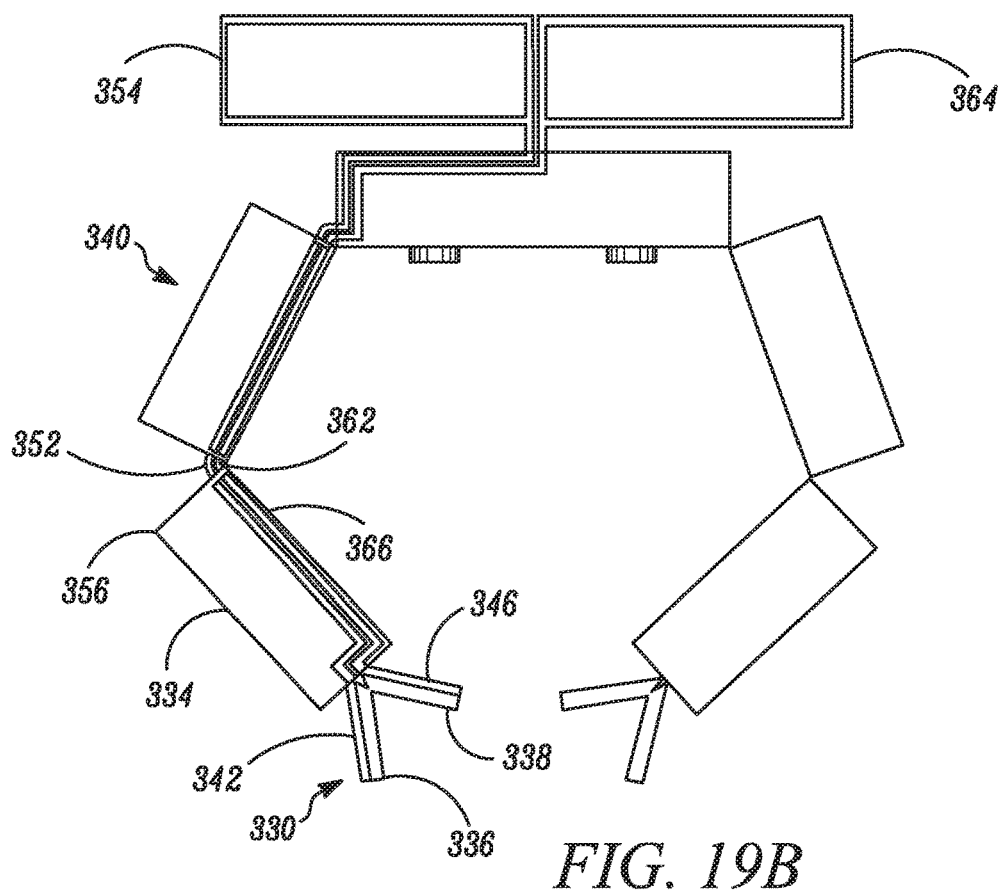
FIG. 19B is a schematic view of a robotic device including the operational component shown in FIG. 19A.

FIG. 19A is a close-up schematic view of an operational component 330 according to one embodiment. As shown in FIGS. 19A and 19B, the operational component 330 is a grasper (also referred to herein as "forceps") operably coupled to a distal end 332 of an arm 334 of an exemplary robotic device 340. According to one implementation, the forceps 330 are commercially-available forceps 330, such as the forceps available from U.S. Surgical, a subsidiary of Covidien, located in North Haven, Conn.

As shown best in FIG. 19A, the grasper 330 includes a first arm 336 and a second arm 338. In this embodiment, the first arm 336 includes an irrigation component 342 coupled to the arm 336 including a nozzle 344 and providing for irrigation with a liquid by ejecting the liquid from the nozzle 344. In addition, the second arm 338 includes a suction component 346.

In one implementation, the irrigation component 342 and suction component 346 are both thin-walled conduits made of a polymer. For each component 342, 346, the conduit (also referred to herein as "tubing") can be commercially available extruded tubing of various sizes depending on the specific application. Methods or techniques for attaching the conduit 342, 346 to the grasper 330 can include any appropriate fasteners or adhesives. According to one embodiment, the nozzle 344 can be a commercially available nozzle, or alternatively can be a specifically designed nozzle that directs the fluid flow as needed.

In accordance with a further alternative embodiment, each of the suction 346 and irrigation 342 components are manufactured as part of the grasper arms 336, 338. More specifically, the suction component 346 is an integral component of and/or is manufactured as a part of the grasper arm 338, while the irrigation component 342 is an integral component of and/or is manufactured as a part of the grasper arm 336. For example, according to one implementation, the conduits could be formed in the structure of the grasper arms 336, 338 such that the conduits do not protrude from the side of the arms 336, 338. Alternatively, the grasper arms 336, 338 could be molded such that the conduits are disposed within the arms 336, 338. For example, the arm and conduit can be manufactured using stainless steel through a metal injection molding process. In a further alternative, the conduits could be machined into the arms 336, 338 by any traditional machining techniques. In yet another alternative, the grasper arm 336, 338 and conduit are manufactured using a polymer-based rapid prototyping method such as stereolithography. Alternatively, the conduits could be formed in the structure of the arms 336, 338 by any known technique.

FIG. 19B provides a complete view of the robotic device 340 to which the operational component 300 is coupled. As shown in FIG. 19B, the irrigation component 342 has an irrigation connection component 352 (also referred to as an "irrigation line" or "irrigation tube") that is connected at one end to the component 342 and at the other end to a liquid source 354. According to one embodiment, the irrigation connection component 352 is a thin-walled conduit made of a polymer. In embodiments in which the irrigation component 342 is a part of the grasper arm 336, the polymer conduit of the connection component 352 connects or couples to the irrigation component 342 at a proximal end 356 of the grasper arm 26.

In some embodiments, as shown in FIG. 19B, the liquid source 354 is an external liquid source 354 and is disposed at a location or position that is external to the robotic device 340. A pump (not shown) is also provided to power the irrigation component 342. In one embodiment, the pump can be a commercially-available surgical irrigation pump such as those available from Nellcor (a subsidiary of Covidien) or KMC Systems which is located in Merrimack, N.H. The pump, and thus the irrigation component 342, can be controlled by a controller (not shown) or microprocessor, which can be associated with or coupled to the pump. The controller or microprocessor may be associated with or connected to the pump via a wired or wireless connection.

In other embodiments, the liquid source 354 can be associated with, incorporated into, or disposed within the robotic device 340. In one embodiment, a pump can be operatively coupled to the liquid source 354. The pump can be a mechanical bellow, a mechanical pump, or any known pump suitable for use with an irrigation system such as any of the irrigation embodiments disclosed herein. In still other embodiments, the liquid source 354 is a pressurized reservoir that does not require an auxiliary pump.

According to a further embodiment, the irrigation component 354 can be used to deliver a drug or combination of drugs to the procedure site or other site within a patient's body as designated by the clinician. The drugs or any other type of treatment composition can be provided in fluid or gel form or any other form that can be injected via a delivery device. In one embodiment, these drugs could include chemotherapy drugs.

As also shown in FIG. 19B, the suction component 346 has a suction connection component 362 connected to the component 346 and further connected to a suction source 364. According to one embodiment, the suction connection component 362 is a thin-walled conduit made of a polymer. In embodiments in which the suction component 346 is a part of the grasper arm 338, the polymer conduit of the connection component 362 connects or couples to the suction component 346 at a proximal end 366 of the grasper arm 28.

In one embodiment, as shown in FIG. 19B, the suction source 364 is an external suction source 364 and is disposed at a location or position that is external to the robotic device 340. A pump (not shown) is also provided to power the suction source 364. According to one embodiment, the pump is a commercially-available aspiration suction unit such as the devices available from Paragon Medical, located in Pierceton, Ind. The pump, and thus the suction component 346, can be controlled by a controller or microprocessor (not shown), which can be associated with or coupled to the pump by a wired or a wireless connection. In other embodiments, the suction source 64 can be associated with, incorporated into, or disposed within the robotic device 340. In one embodiment, a pump is coupled to the suction source. The pump can be a mechanical bellow, a mechanical pump, or any known pump for use with a suction system such as any of the suction embodiments disclosed herein. In still other embodiments, the suction source is a vacuumed reservoir that does not require an additional pump.

Figure 20A:
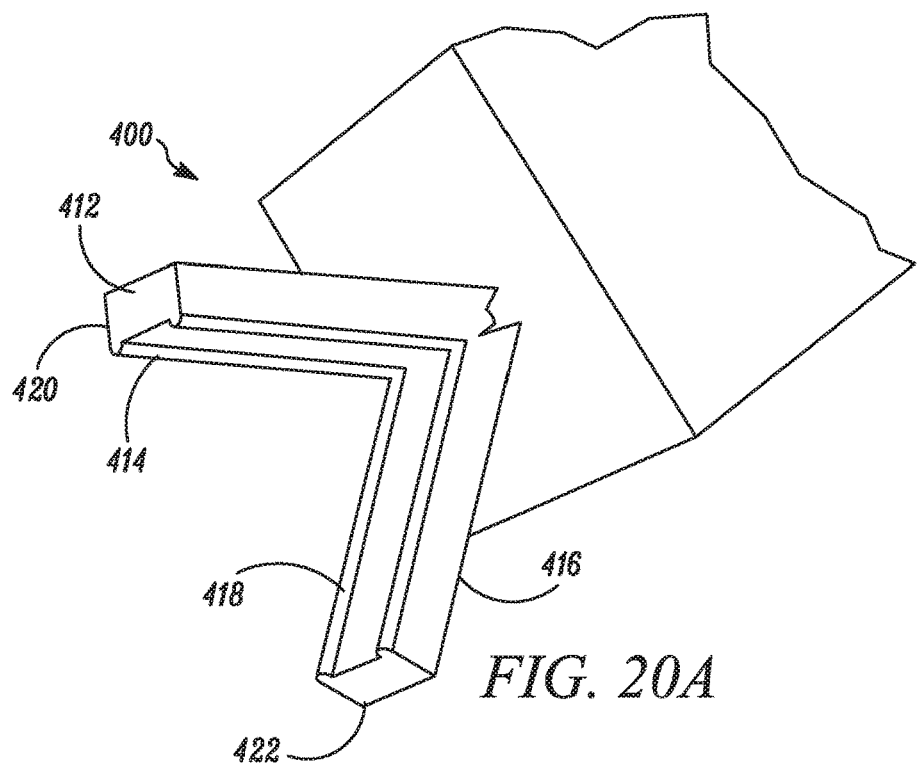
FIG. 20A is a close-up, schematic view of an operational component according to one embodiment.
Figure 20B:
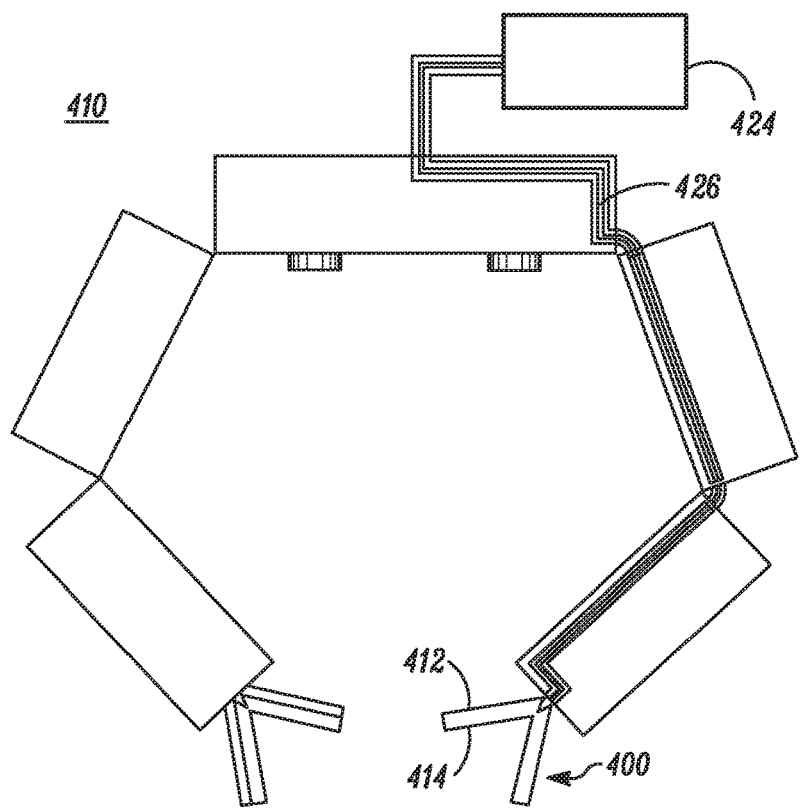
FIG. 20B is a schematic view of a robotic device including the operational component shown in FIG. 20A.

FIGS. 20A and 20B depict another embodiment of a grasper 400 of a robotic device 410 in which the first arm 412 includes a cautery component 414 coupled with or integrated into the first arm 412. According to one embodiment, the cautery component 414 is a wire 414 coupled to the first arm 412. The cautery component 414 can be any wire 414 having a large electrical resistance such that it is heated by passing an electrical current through the wire 414. In one embodiment, the cautery wire 414 is composed of a metal alloy that provides a very high electrical resistance. One example of the composition of the wire 414 is commercially-available 80/20 Nickel-Chrome alloy (80% Nickel, and 20% Chrome).

According to some embodiments, as shown in FIG. 20A, the second arm 416 of the grasper 400 can also include a cautery component 418. In some embodiments, only one of the two arms 412, 416 has a cautery component.

In one implementation, the cautery wire 414 and/or 418 is secured to the grasper arm 412 and/or 416 using high-temperature adhesives or mechanical fasteners. In another embodiment, the arms 412, 416 of the grasper 400 are metal injection molded and the cautery wire 414 and/or 416 is molded into the arm 52. In one embodiment, the cautery component 414 and/or 416 can be attached to the inside of the arm 412 and/or 416, or along the side or bottom of the grasper arm 412 and/or 416, depending on the specific application. In a further embodiment, the cautery component 414 and/or 416 can be attached to a distal tip 420 and/or 422 of the arm 412 and/or 414.

An insulation component (not shown) is provided in certain embodiments between the cautery component 414 and the first arm 412, thereby electrically isolating the cautery component 414 from the first arm 412 and preventing the arm 412 from acting as a heat sink or otherwise reducing the effectiveness of the cautery component 414. A similar configuration can also be provided for the cautery component 418 on the second arm 416 when such a cautery component 418 is provided.

FIG. 20B provides a complete view of the robotic device 410 to which the operational component 400 is coupled. As shown in FIG. 20B, the cautery component 414 is coupled to an external power source 424 via an electrical connection 426 that runs through the robotic device 410. In this embodiment, while the cautery component 414 can be a high resistance wire 414, the electrical connection 426 connecting the component 400 to the power source 424 is not a high resistance wire. The external power source 424 can be any power source that is positioned at a location external to the robotic device 410. In one exemplary embodiment, the power source 424 is a battery. Alternatively, the power source 424 can be associated with, incorporated into, or disposed within the robotic device 410.

According to some embodiments, a controller or microprocessor (not shown), is provided for control of the cautery component 414. In one embodiment, the controller can be a switch that is positioned on the external power source 424. In other embodiments, the controller can be a separate component that is coupled to the power source 424 via a wired or a wireless connection. In implementations in which the power source 424 is an internal power source, the controller is provided as a separate component.

Figure 20C:
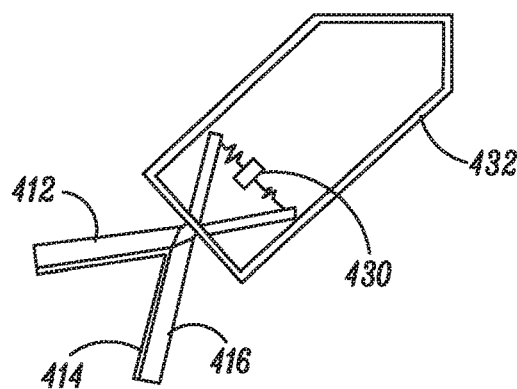
FIG. 20C is a close-up schematic view of an operational component according to an embodiment.

In some embodiments, there is no need for actuating the cautery component 414 with a switch or other type of separate cautery controller. For example, the cautery component 414 depicted in FIG. 20C is actuated when the grasper arms 412, 416 are positioned within a certain proximity of each other. In this embodiment, as the grasper arms 412, 416 are moved closer to each other and pass a predetermined threshold, the cautery component 414 is actuated. According to one embodiment, this functionality is accomplished with a sensor 430. The sensor 430 senses the positioning of the arms 412, 416 and actuates the power source (not shown) when the arms 412, 416 pass a predetermined location or position. In one embodiment, the sensor 430 is positioned in the robotic arm 432 and operatively coupled to the grasper arms 412, 416 as depicted. Alternatively, the sensor 730 can also be positioned on one of the grasper arms 412, 416.

In one embodiment, the sensor 430 is a commercially-available infrared sensor. For example, the sensor 430 could be a sensor such as the sensors manufactured by Fairchild Semiconductor, located in South Portland, Me. Alternatively, the sensor 430 is a commercially-available rotational or translational variable resistance potentiometer.

Figure 21A:
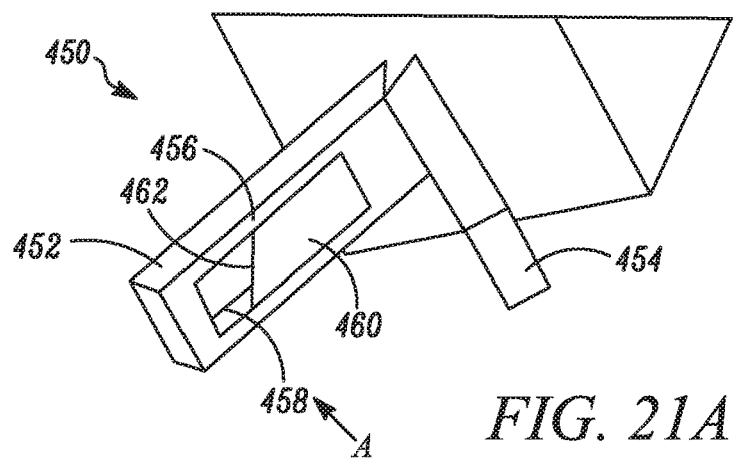
FIGS. 21A-21C are close-up, schematic views of an operational component according to various embodiments.
Figure 21B:
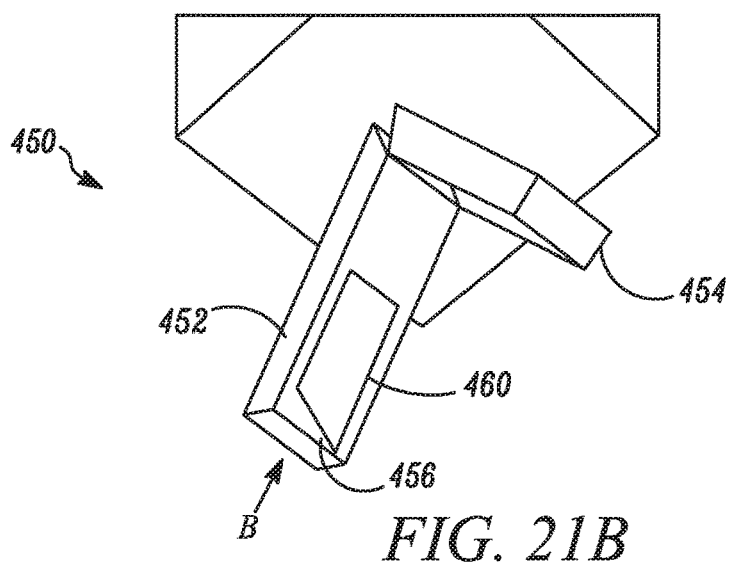
Figure 21C:
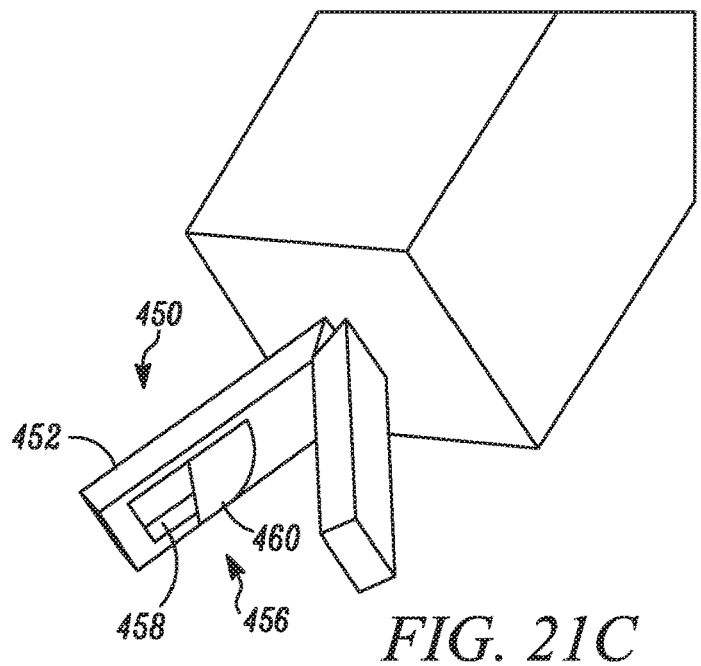

According to another implementation, the multifunctional operational component can be a biopsy component. For example, FIGS. 21A, 21B, and 21C depict a grasper 450 including a first arm 452 and a second arm 454. The first arm 452 includes a biopsy component 456. In other embodiments, both grasper arms 452, 454 include a biopsy component such that more than one tissue sample can be taken. In still another embodiment, one or both of the arms 452, 454 can include more than one biopsy component.

In one implementation, the biopsy component includes a reservoir 458 and a cutting tool 460. The cutting tool can be a knife blade, a rotary cutter, or other cutting instrument. In the implementation depicted in FIGS. 21A and 21B, the knife 460 is slidable between a closed and an open position. In the closed position, the cutting tool 460 is positioned to cover the reservoir 458 and thereby act as a lid or cover for the reservoir 458. In the open position, the cutting tool 460 is positioned adjacent to the reservoir 458 with the cutting edge 462 adjacent to the reservoir 458.

In use, according to one embodiment, the cutting tool 460 can be used to obtain a biopsy sample in the following manner. The cutting tool 460 is positioned or urged into the open position (position A as shown in FIG. 21A). In this position, the reservoir 458 is exposed or open. The arms 452, 454 can then be used to grasp or otherwise be positioned with respect to a specimen of interest such that the cutting tool 460 can then be urged or otherwise moved toward the closed position B. As the cutting tool 460 moves toward the closed position B, the cutting edge 462 contacts the specimen of interest and cuts the specimen. Then, as the cutting tool 460 reaches the closed position B (shown in FIG. 21B), the cut portion of the specimen is positioned in the reservoir 458 and the cutting tool 460 is positioned in the closed position B, thereby closing the opening of the reservoir 458 and retaining the cut specimen in the reservoir 458.

In another embodiment, the cutting tool 460 and the reservoir cover or lid are separate components in which the cutting tool 460 is used to cut the specimen and the cover or lid is used to cover or close the reservoir 448.

According to the embodiments depicted in FIGS. 21A and 21B, the cutting tool 90 travels between position A and position B along a track (not shown) that is formed into or associated with the grasper arm 452. In another embodiment, the cutting tool 460 can operate by rotating in a plane parallel with the grasper face as shown in FIG. 21C.

According to some embodiments, the biopsy component 456 can include a cutting tool actuation component (not shown). The cutting tool actuation component can be a pre-loaded spring or series of pre-loaded springs that move between a coiled or tensioned position and an uncoiled or released position to actuate the cutting tool to slide shut over the reservoir. For example, in one embodiment, the pre-loaded spring is operably coupled to a switch (not shown) positioned either in the grasper 450 or the robotic arm to which the grasper 450 is coupled. The switch releases the spring from its coiled or tensioned position. Thus, actuating the switch releases the spring and urges the cutting tool 460 to slide shut over the reservoir. This switch can be an SMA (shape memory alloy) or solenoid coil. Actuation of the switch allows the pre-loaded springs to push against the cutting tool 460, thereby urging the cutting tool 460 to move between the open and closed positions.

In another embodiment, the pre-loaded spring or springs could be mechanically triggered when the grasper arms are sufficiently closed. Alternatively, the cutting tool actuation component could be coupled to the grasper 450. In this embodiment, when the biopsy component 450 is engaged, the cutting tool is actuated as the grasper arms 452, 454 are closed. In still other embodiments, the cutting tool 460 could be actuated by a small onboard motor and lead screw.

Figure 22:
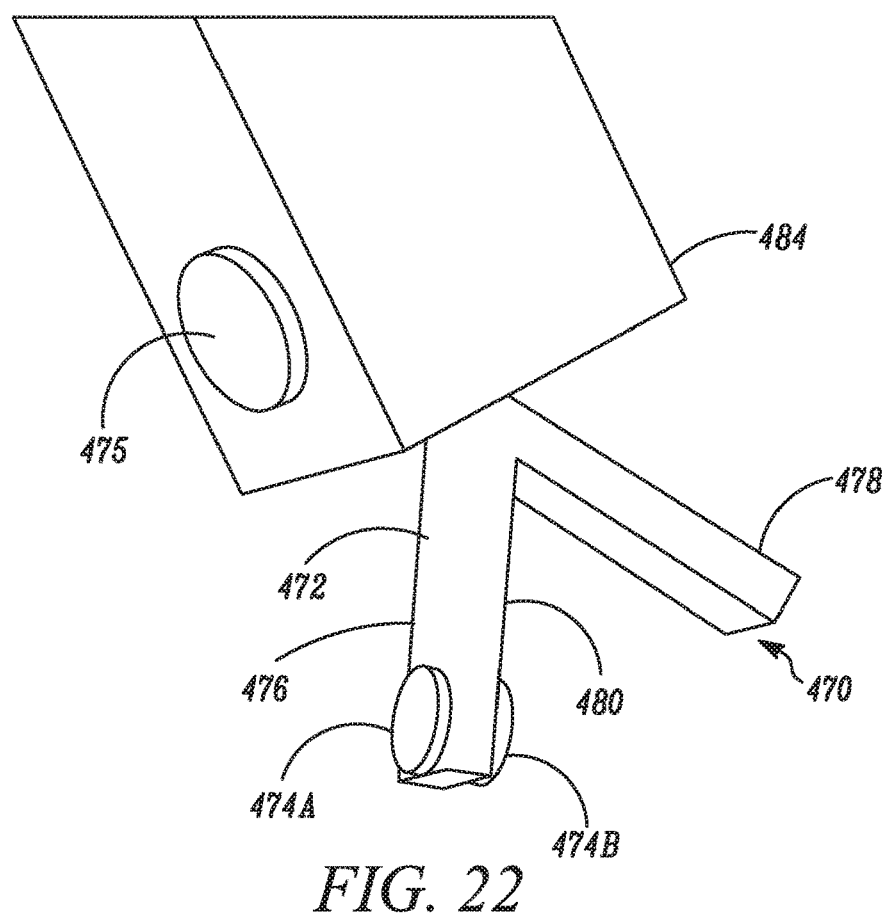
FIG. 22 is a close-up, schematic view of an operational component according to an embodiment.

FIG. 22 depicts yet another embodiment of a grasper 470 in which the first arm 472 is equipped with at least one sensor 474. The sensor 474A is positioned on the back side 476 (away from the other grasper arm 478) of the grasper arm 472. A second sensor 474B is positioned on the front side 480 (toward the other arm) of the grasper arm 472. The first and second sensors 474A and 474B can be the same or different type of sensor. In a further embodiment, a single sensor can be provided and positioned on either side of the arm 472. In yet another embodiment, another sensor 475 can be positioned on or otherwise coupled to the robotic arm 484.

In one embodiment, each sensor 474A, 474B comprises an electronics package that includes a commercially-available sensor solid state chip (pH, humidity, pressure, temperature, etc.) and supporting capacitors and resistors. This electronics package is electrically connected to the main circuit board (not shown) in the robotic device base and the sensor readings are transmitted to an external display either in a wireless or wired fashion. This package can be placed in the robot arm 484 or in the grasper 470 so that each sensor 474A, 474B is exposed to the environment around the robotic device.

Figure 23:
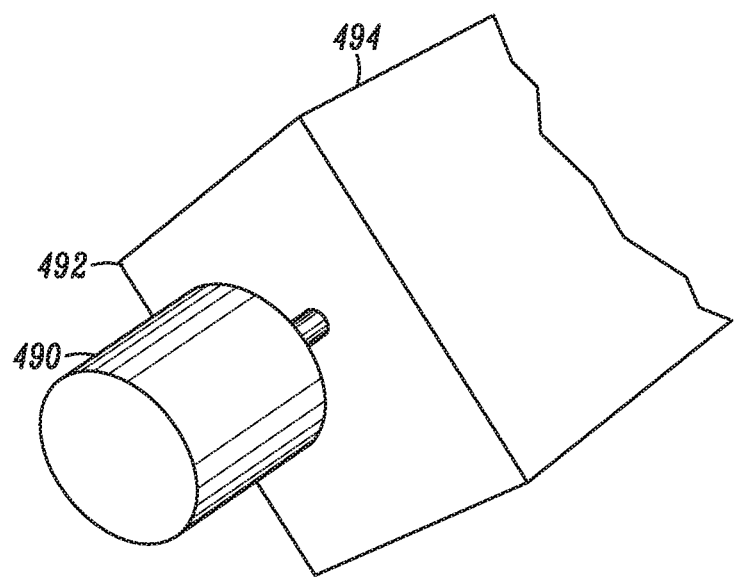
FIG. 23 is a close-up, schematic view of an operational component according to one embodiment.

FIG. 23 is a close-up schematic view of an operational component 490 according to yet another embodiment. The operational component 490 is a sensor 490 and is coupled to a distal end 492 of an arm 494 of a robotic device (not shown). The sensor 490 can be any sensor capable of detecting a physiological parameter within a patient's body including, but not limited to pH, humidity, pressure, or temperature. In some embodiments, the sensor 490 is capable of detecting all or some combination of those parameters.

The sensor can be configured in any known fashion using known components. The supporting electronics can include resistors, capacitors, and oscillators that are used to drive the sensors. Output from these sensors will be a data stream transmitted to the external console either wirelessly, or through the tether cable connected to the robot. In these embodiments, the power can be supplied by a battery. In another embodiment, the power and non-essential supporting electronics can be provided in a location external to the patient so that only the sensor is onboard. According to one embodiment, power requirements for the various sensors can be met with power supplied from a standard wall outlet. Such power can be down-regulated through power regulators in the console that connect with the robotic device.

In yet another embodiment, the sensor 490 can be an ultrasound transducer including a transmitter and receiver, or an infrared transducer including a transmitter and receiver. The ultrasound transducer 490 can be a commercially-available system that is routinely used at the tip of an endoscope, which is commonly referred to as Endoscopic Ultrasound ("EUS"). In the standard technologies, placing the transducer on the tip of an endoscope allows the transducer to get close to the organs inside the body. Because of the proximity of the EUS transducer to the organ(s) of interest, the images obtained are frequently more accurate and more detailed than the ones obtained by traditional ultrasounds. Attaching the ultrasound transducer 490 to the distal end 492 of the robotic arm 494 of one embodiment of the various devices disclosed herein allows even greater access to the organ of interest. In some embodiments, the supporting electronics can be positioned inside the robotic arm 494 or elsewhere in the robotic device. In other embodiments, the supporting sensor electrics may be located external to the patient, while only the ultrasonic transducer 490 is provided onboard the robotic device.

Figure 24:
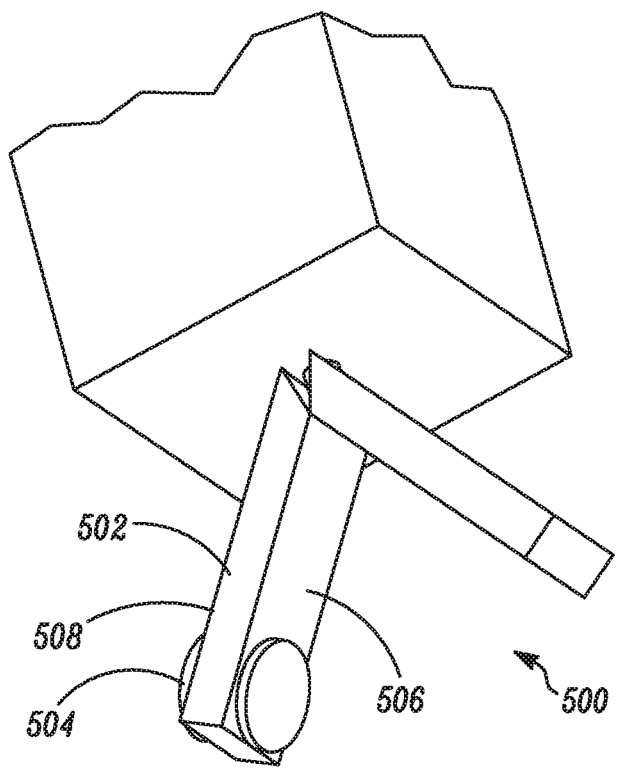
FIG. 24 is a close-up, schematic view of an operational component according to one embodiment.

FIG. 24 depicts another embodiment of a grasper 500 including at least a first arm 502 equipped with at least one treatment module 504. The treatment module 504 can be provided either on the front side 506 or the back side 508 of the grasper arm 502 or both, as shown. Alternatively, more than one treatment module 504 can be provided in any configuration. If more than one treatment module is provided, the treatment modules 504 can have the same or different functions as one another.

Figure 25:
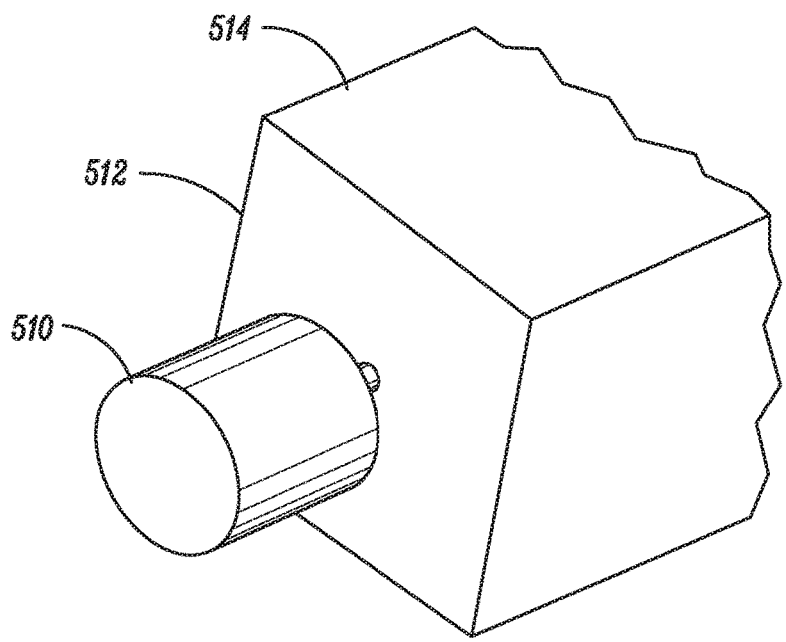
FIG. 25 is a close-up, schematic view of an operational component according to one embodiment.

In another embodiment depicted in FIG. 25, an operational module 510 that is a treatment module can be coupled directly to a distal end 512 of the robotic device arm 514. According to certain embodiments, the treatment module 510 can provide, but is not limited to providing, treatment at the site of interest through the use of RF (radio frequency) ablation, microwave ablation, and ultrasonic ablation. In one embodiment, the treatment module 510 is a commercially-available microware or ultrasonic ablation transducer used commonly in catheter-based systems.

According to one implementation, any one of the robotic devices discussed herein can have a power source and/or a processing unit to operate any embodiment of a treatment module such as the treatment module described above. In one embodiment, the power source and/or processing unit are disposed within, attached to, or otherwise associated with the device. According to one embodiment, the power source is a battery. In another embodiment, the power source and data processing can be positioned in a location external to the robotic device so that only the treatment module, and any essential supporting electronics, is coupled to the robotic device.

In one embodiment, the mechanical and electrical couplings between the modular robotic sections are universal to help facilitate ease of assembly. That is, the couplings or connections are universal such that the various modules can be easily and quickly attached or removed and replaced with other modules. Connections can include friction fits, magnets, screws, locking mechanisms and sliding fitting. Alternatively, the connections can be any known connections for use in medical devices. In use, the couplings can be established by the surgeon or user according to one implementation. Alternatively, the couplings can be semi-automated such that the components are semi-self-assembling to improve timeliness.

Modular components need not be arms or other types of components having operational components or end effectors. According to various alternative embodiments, the modular components can be modular mechanical and electrical payload packages that can be used together in various combinations to provide capabilities such as obtaining multiple tissue samples, monitoring physiological parameters, and wireless command, control, and data telemetry. It is understood that the modular payload components can be incorporated into all types of medical devices, including the various medical devices discussed and incorporated herein, such as magnetically controllable devices and/or wheeled devices similar to those disclosed in the applications incorporated above.

Figure 26A:
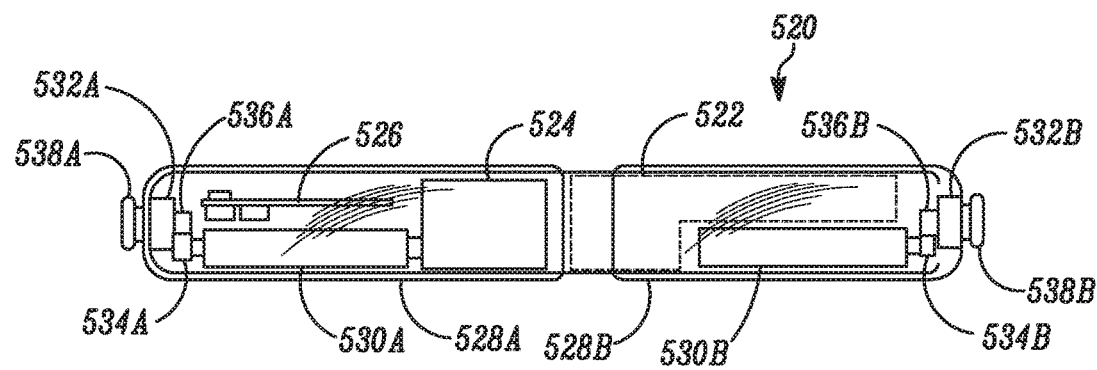
FIG. 26A is a front view of a modular medical device with a payload space, according to one embodiment.

FIG. 26A shows one embodiment of a device 520 having a payload area 522 that can accommodate various modular components such as environmental sensors, biopsy actuator systems, and/or camera systems. More specifically, the payload area 522 is configured to receive any one of several modular components, including such components as the sensor, controller, and biopsy components discussed herein. It is understood that in addition to the specific modular components disclosed herein, the payload areas of the various embodiments could receive any known component to be added to a medical procedural device.

It is further understood that the robotic device having the payload area can be any known robotic device, including any device that is positioned substantially adjacent to or against a patient cavity wall (such as via magnetic forces), and is not limited to the robotic devices described in detail herein. Thus, while the robotic device embodiments depicted in FIGS. 26A and 26B (discussed below) are mobile devices having wheels, the various modular components described herein could just as readily be positioned or associated with a payload area in any other kind of robotic device or can further be used in other medical devices and applications that don't relate to robotic devices.

Returning to FIG. 26A, in this embodiment, the device is not tethered and is powered by an onboard battery 524. Commands can be sent to and from the device using an RF transceiver placed on a circuit board 526. Alternatively, the device 520 can be tethered and commands and power can be transmitted via the tether.

In the embodiment of FIG. 26A, the wheels 528A and 528B are powered by onboard motors 530A and 530B. Alternatively, the wheels 528A, 528B and other components can be actuated by any onboard or external actuation components. The wheels 528 in this implementation are connected to the motors 530 through a bearing 532 and a set of spur gears 534 and 536. Alternatively, any known connection can be used. The use of independent wheels allows for forward, reverse, and turning capabilities. In this embodiment, a small retraction ball 538 is attached to the outside of each wheel for retraction using a surgical grasper. Alternatively, no retraction component is provided. In a further alternative, any known retraction component can be included.

Figure 26B:
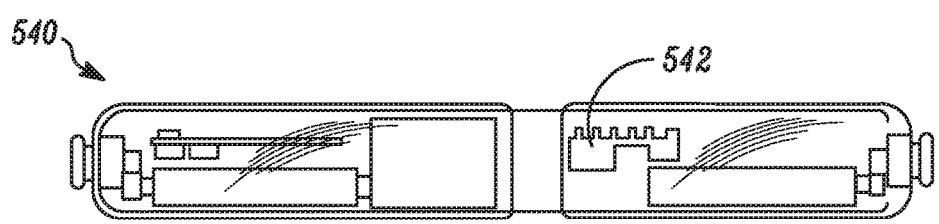
FIG. 26B is another front view of the device of FIG. 26A.

FIG. 26B shows yet another embodiment of a device 540 having a payload area 542. In this embodiment, the modular component in the payload area 542 is a sensor component. It is further understood that, according to various other implementations, more than one modular component can be positioned in the payload area 542 of this device 540 or any other device having a payload area. For example, the payload area 542 could include both a biopsy component and a sensor component, or both a biopsy component and a controller component. Alternatively, the payload area 542 could include any combination of any known functional components for use in procedural devices.

In accordance with one implementation, one component that can be included in the payload area 542 is a sensor package or component. The sensor package can include any sensor that collects and/or monitors data relating to any characteristic or information of interest. In one example, the sensor package includes a temperature sensor. Alternatively, the package includes an ambient pressure sensor that senses the pressure inside the body cavity where the device is positioned. In a further alternative, the package can include any one or more of a relative humidity sensor, a pH sensor, or any other known type of sensor for use in medical procedures.

The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

FIGS. 27A-32 depict a multi-segmented medical device 550, in accordance with one implementation. According to one embodiment, the device 550 is a robotic device 550 and further can be an in vivo device 550. This device embodiment 550 as shown includes three segments 552A, 552B, 554. Segments 552A and 552B are manipulator segments, while segment 554 is a command and imaging segment. Alternatively, the three segments can be any combination of segments with any combination of components and capabilities. For example, according to an alternative embodiment, the device could have one manipulator segment, one command and imaging segment, and a sensor segment. In a further alternative, the various segments can be any type of module, including any of those modules described above with respect to other modular components discussed herein.

Figure 27A:
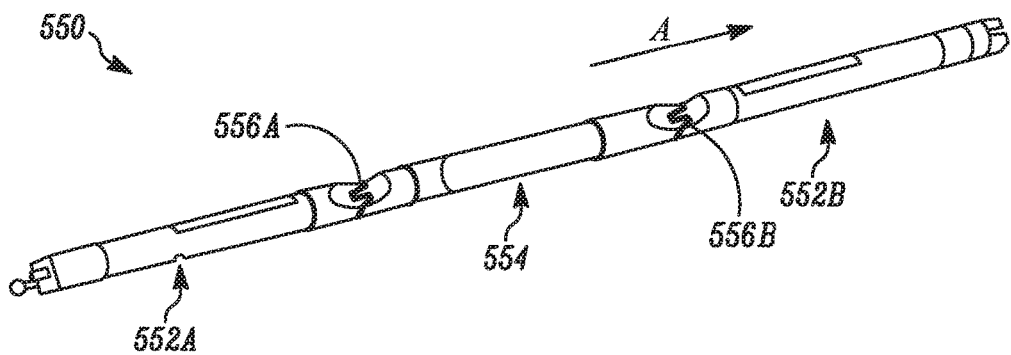
FIG. 27A is a perspective view of a modular medical device, according to another embodiment.
Figure 27B:
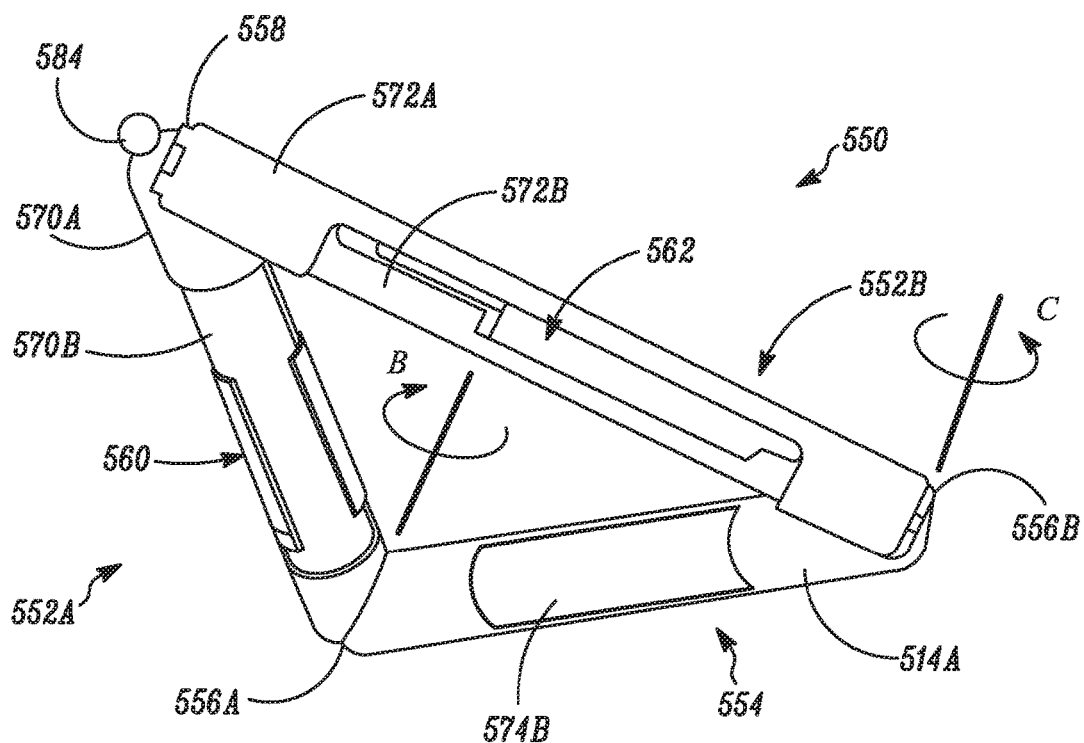
FIG. 27B is a perspective bottom view of the device of FIG. 27A.

As best shown in FIGS. 27A and 27B, segments 552A, 552B are rotatably coupled with the segment 554 via joints or hinges 556A, 556B. More specifically, segment 552A is rotatable relative to segment 554 about joint 556A around an axis as indicated by arrow B in FIG. 27B, while segment 552B is rotatable relative to segment 554 about joint 556B around an axis as indicated by arrow C in FIG. 27B.

In accordance with one embodiment, the device 550 has at least two configurations. One configuration is an extended or insertion configuration as shown in FIG. 27A in which the three segments 552A, 552B, 554 are aligned along the same axis. The other configuration is a triangle configuration as shown in FIG. 27B in which the manipulator segments 552A, 552B are each coupled to the segment 554 via the joints 556A, 556B and further are coupled to each other at a coupleable connection 558 at the ends of the segments 552A, 552B opposite the joints 556A, 556B.

Figure 28A:
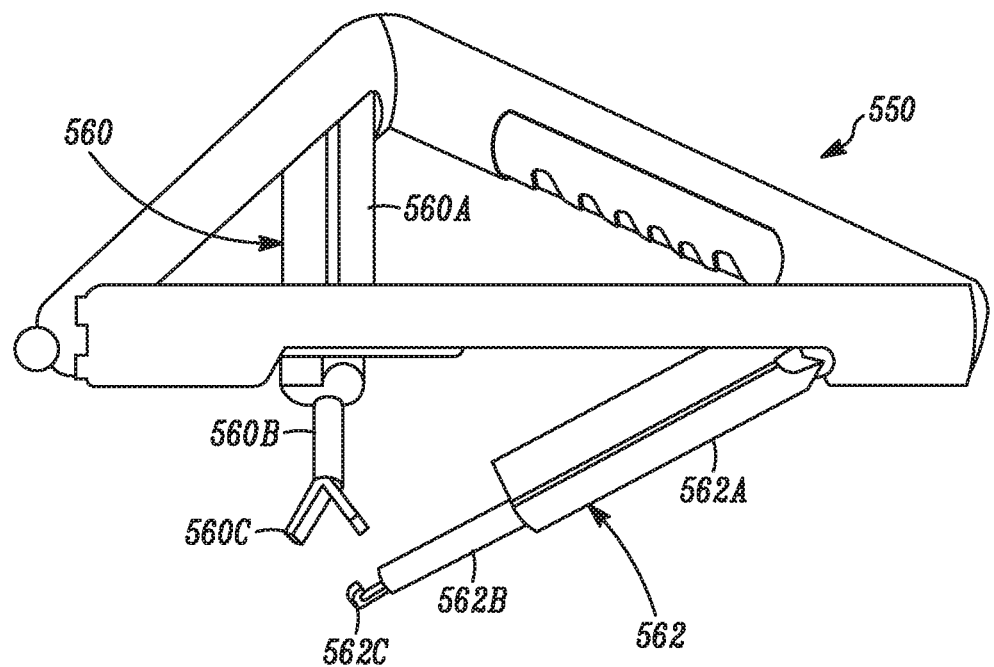
FIG. 28A is a perspective top view of the device of FIG. 27A.
Figure 29:
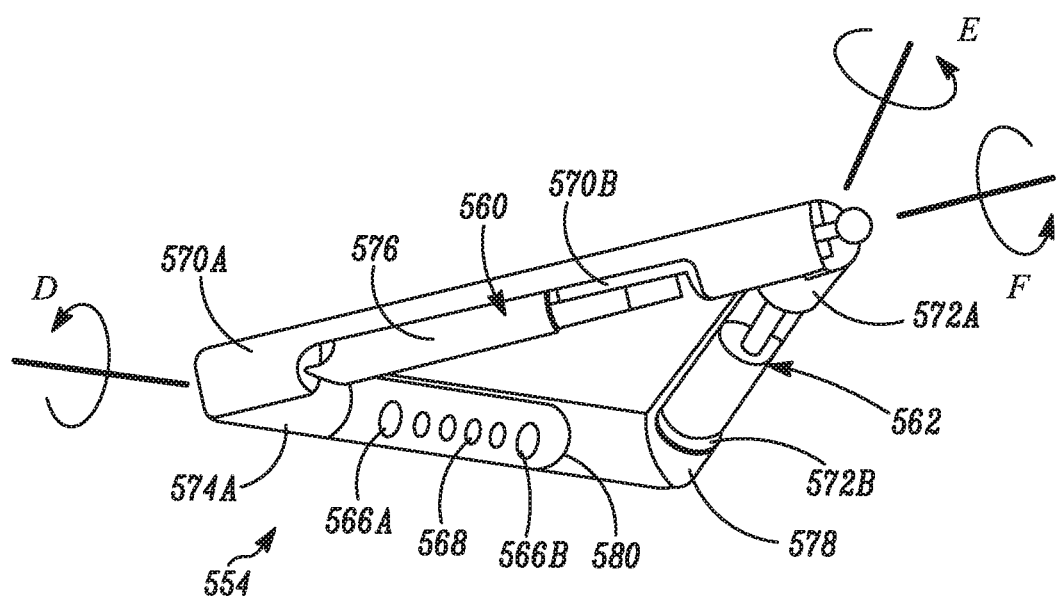
FIG. 29 is a perspective bottom view of the device of FIG. 27A.
Figure 30:
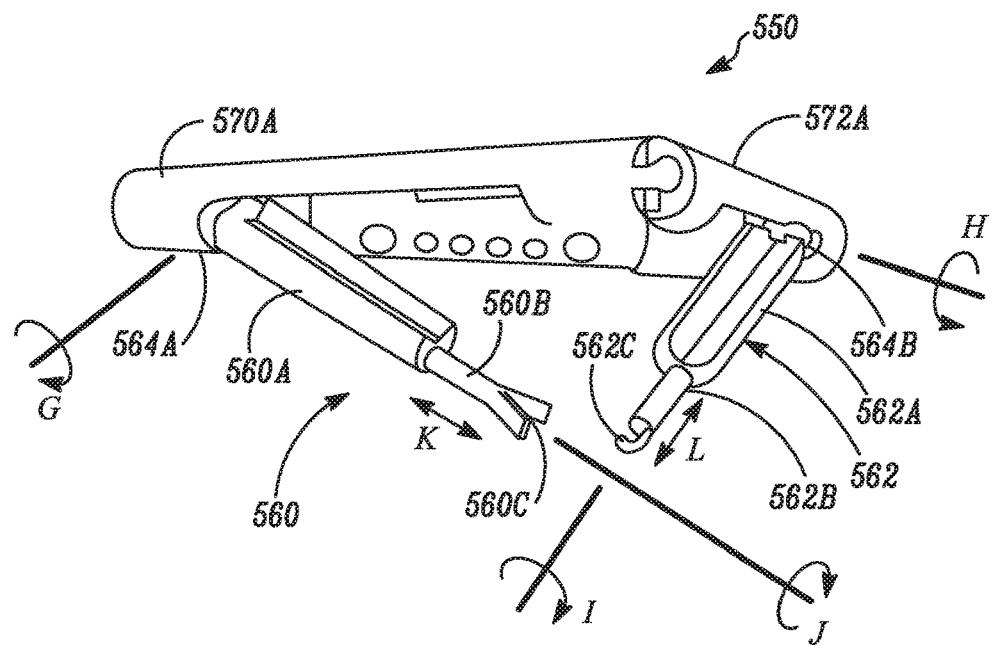
FIG. 30 is a perspective side view of the device of FIG. 27A.

As best shown in FIG. 28A, each of the manipulator segments 552A, 552B in this particular embodiment has an operational arm 560, 562 (respectively). Each arm 560, 562 is moveably coupled to its respective segment 552A, 552B at a joint 564A, 564B (respectively) (as best shown in FIG. 30). Further, segment 554 has a pair of imaging components (each also referred to herein as a "camera") 566A, 566B (as best shown in FIG. 29).

In one embodiment, each arm 560, 562 is configured to rotate at its joint 564A, 564B in relation to its segment 552A, 552B to move between an undeployed position in which it is disposed within its segment 552A, 552B as shown in FIG. 27B and a deployed position as shown in FIG. 28A. In one example, arm 560 is rotatable relative to segment 552A about joint 564A in the direction shown by G in FIG. 30, while arm 562 is rotatable relative to segment 552B about joint 564B in the direction shown by H in FIG. 30. Alternatively, the arms 560, 562 are moveable in relation to the segments 552A, 552B in any known fashion and by any known mechanism.

According to one embodiment as best shown in FIG. 28A, each arm 560, 562 has three components: a proximal portion 560A, 562A, a distal portion 560B, 562B, and an operational component 560C, 562C coupled with the distal portion 560B, 562B, respectively. In this embodiment, the distal portion 560B, 562B of each arm 560, 562 extends and retracts along the arm axis in relation to the proximal portion 560A, 562A while also rotating around that axis in relation to the proximal portion 560A, 562A. That is, distal portion 560B of arm 560 can move back and forth laterally as shown by the letter K in FIG. 30 and further can rotate relative to the proximal portion 560A as indicated by the letter J, while distal portion 562B of arm 562 can move back and forth laterally as shown by the letter L in FIG. 30 and further can rotate relative to the proximal portion 562A as indicated by the letter I.

In accordance with one implementation, the operational components 560C, 562C (also referred to herein as "end effectors") depicted in FIG. 28A are a grasper 560C and a cautery hook 562C. It is understood that the operational component(s) used with the device 550 or any embodiment herein can be any known operational component for use with a medical device, including any of the operational components discussed above with other medical device embodiments and further including any operational components described in the applications incorporated above. Alternatively, only one of the two arms 560, 562 has an operational component. In a further alternative embodiment, neither arm has an operational component.

Alternatively, each arm 560, 562 comprises one unitary component or more than two components. It is further understood that the arms 560, 562 can be any kind of pivotal or moveable arm for use with a medical device which may or may not have operational components coupled or otherwise associated with them. For example, the arms 260, 262 can have a structure or configuration similar to those additional arm embodiments discussed elsewhere herein or in any of the applications incorporated above. In a further alternative, the device 550 has only one arm. In a further alternative, the device 550 has no arms. In such alternative implementations, the segment(s) not having an arm can have other components associated with or coupled with the segment(s) such as sensors or other types of components that do not require an arm for operation.

As discussed above, the segment 554 of the embodiment depicted in FIG. 29 has a pair of cameras 566A, 566B. Alternatively, the segment 554 can have a single camera or two or more cameras. It is understood that any known imaging component for medical devices, including in vivo devices, can be used with the devices disclosed herein and further can be positioned anywhere on any of the segments or on the arms of the devices.

In a further embodiment, the segment 554 as best shown in FIG. 29 can also include a lighting component 568. In fact, the segment 554 has four lighting components 568. Alternatively, the segment 554 can have any number of lighting components 568 or no lighting components. In a further alternative, the device 550 can have one or more lighting components positioned elsewhere on the device, such as one or both of segments 552A, 552B or one or more of the arms, etc.

In accordance with a further embodiment as best shown in FIGS. 27B and 29, each of the segments 552A, 552B, 554 has two cylindrical components—an outer cylindrical component and an inner cylindrical component—that are rotatable in relation to each other. More specifically, the segment 552A has an outer cylindrical component 570A and an inner cylindrical component 570B that rotates relative to the outer component 570A around an axis indicated by arrow F in FIG. 21. Similarly, the segment 552B has an outer cylindrical component 572A and an inner cylindrical component 572B that rotates relative to the outer component 572A around an axis indicated by arrow E in FIG. 29. Further, the segment 554 has an outer cylindrical component 574A and an inner cylindrical component 574B that rotates relative to the outer component 574A around an axis indicated by arrow D in FIG. 29.

In use, the embodiments having rotatable cylindrical components as described in the previous paragraph can provide for enclosing any arms, cameras, or any other operational components within any of the segments. Further, any segment having such rotatable components provide for two segment configurations: an open configuration and a closed configuration. More specifically, segment 552A has an outer cylindrical component 570A with an opening 576 as shown in FIG. 29 through which the arm 560 can move between its deployed and undeployed positions. Similarly, segment 552B has an outer cylindrical component 572A with an opening 578 as shown in FIG. 29 through which the arm 562 can move between its deployed and undeployed positions. Further, segment 554 has an outer cylindrical component 574A with an opening 580 as shown in FIG. 29 through which the imaging component(s) 566A, 566B can capture images of a procedural or target area adjacent to or near the device 550.

FIG. 27B depicts the segments 552A, 552B, 554 in their closed configurations. That is, each of the inner cylindrical components 570B, 572B, 574B are positioned in relation to the respective outer cylindrical component 570A, 572A, 574A such that each opening 576, 578, 580, respectively, is at least partially closed by the inner component 570B, 572B, 574B such that the interior of each segment 552A, 552B, 554 is at least partially inaccessible from outside the segment.

More specifically, in the closed position, inner cylindrical component 570B of segment 552A is positioned in relation to outer cylindrical component 570A such that the arm 560 is at least partially enclosed within the segment 552A. According to one embodiment, the inner cylindrical component 570B is configured such that when it is in the closed position as shown in FIG. 27B, it closes off the opening 576 entirely. In a further embodiment, the inner cylindrical component 570B in the closed position fluidically seals the interior of the segment 552A from the exterior.

Similarly, in the closed position, inner cylindrical component 572B of segment 552B is positioned in relation to the outer cylindrical component 572A such that the arm 562 is at least partially enclosed within the segment 552B. According to one embodiment, the inner cylindrical component 572B is configured such that when it is in the closed position as shown in FIG. 27B, it closes off the opening 578 entirely. In a further embodiment, the inner cylindrical component 572B in the closed position fluidically seals the interior of the segment 552B from the exterior.

Further, in the closed position, inner cylindrical component 574B of segment 554 is positioned in relation to the outer cylindrical component 574A such that the imaging component(s) is not positioned within the opening 580. According to one embodiment, the inner cylindrical component 574B is configured such that when it is in the closed position as shown in FIG. 27B, the imaging component(s) and any lighting component(s) are completely hidden from view and not exposed to the exterior of the segment 554. In a further embodiment, the inner cylindrical component 574B in the closed position fluidically seals the interior of the segment 554 from the exterior.

In contrast, FIGS. 28A and 29 depict the segments 552A, 552B, 554 in their open configurations. In these configurations, each of the inner cylindrical components 570B, 572B, 574B are positioned such that the openings 576, 578, 580 are open.

In use, according to one embodiment, the inner cylindrical components 570B, 572B, 574B can thus be actuated to move between their closed and their open positions and thereby convert the device 550 between a closed or non-operational configuration (in which the operational components such as the arms 560, 562 and/or the imaging components 566 and/or the lighting components 568 are inoperably disposed within the segments 552A, 552B, 554) and an open or operational configuration (in which the operational components are accessible through the openings 576, 578, 580 and thus capable of operating). Thus, according to one implementation, the device 550 can be in its closed or non-operational configuration during insertion into a patient's body and/or to a target area and then can be converted into the open or operational configuration by causing the inner cylindrical components 570B, 572B, 574B to rotate into the open configurations.

Alternatively, one or more or all of the segments do not have inner and outer components that rotate in relation to each other.

It is understood that the various embodiments of the device 550 disclosed herein include appropriate actuation components to generate the force necessary to operate the arms and/or the rotatable cylinders in the segments. In one embodiment, the actuation components are motors. For example, segment 552A has a motor (not shown) operably coupled with the arm 560 and configured to power the movements of the arm 560. Similarly, segment 552B also has a motor (not shown) operably coupled with the arm 562 and configured to power the movements of the arm 560. In further embodiments, each of the segments 552A, 552B, 554 also have motors (not shown) operably coupled to one or both of the inner and outer cylinder of each segment to power the rotation of the cylinders in relation to each other. In one embodiment, each segment can have one motor to power all drivable elements (arms, cylinders, etc.) associated with that segment. Alternatively, a separate motor can be provided for each drivable element.

Figure 28B:
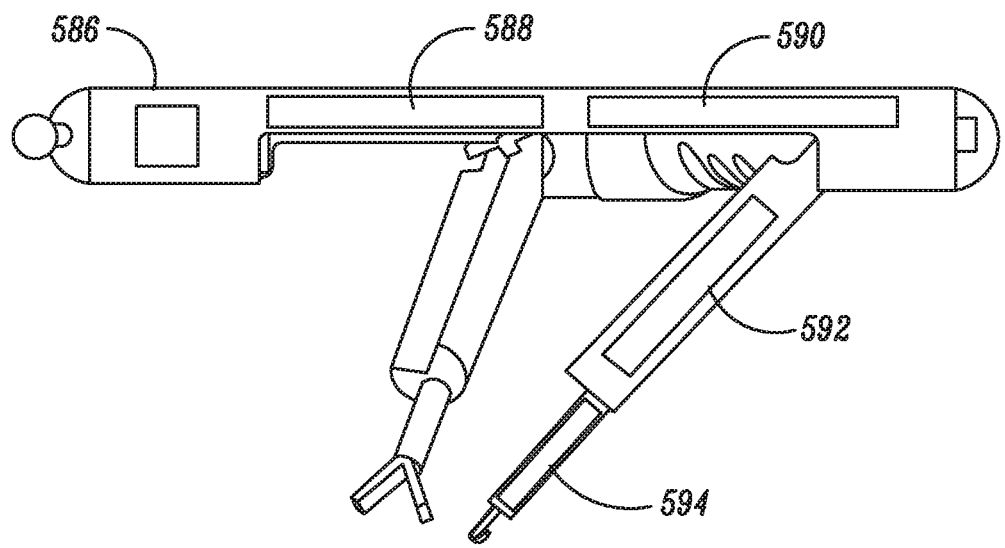
FIG. 28B is a perspective side view of the device of FIG. 27A.
Figure 28C:
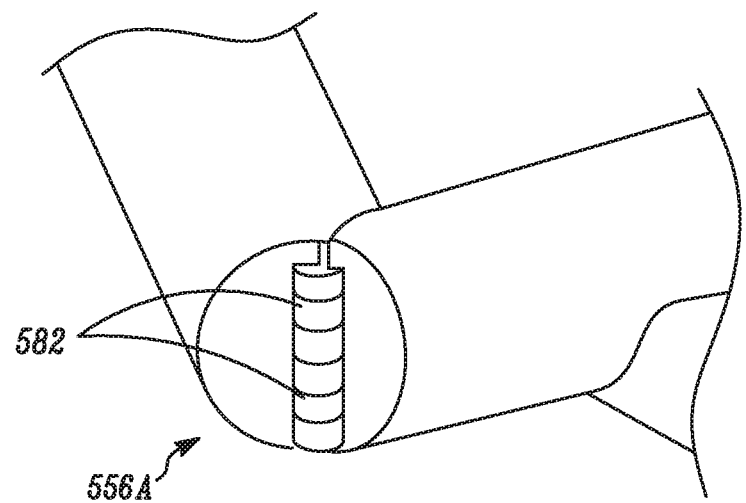
FIG. 28C is a perspective close-up view of a portion of the device of FIG. 27A.

In one embodiment, the joints 556A, 556B are configured to urge the segments 552A, 552B from the insertion configuration of FIG. 27A into the triangular configuration of FIG. 27B. That is, the joints 556A, 556B have torsion springs or some other known mechanism for urging the segments 552A, 552B to rotate around their joints 556A, 556B. For example, FIG. 28C depicts one embodiment in which the joint 556A has torsion springs 582 that are configured to urge segment 552A toward the triangular configuration.

In use, in accordance with one implementation, the device 550 in the insertion configuration as shown in FIG. 27A can be inserted into a patient's body through an incision, a trocar port, or natural orifice in the direction indicated by arrow A. Alternatively, the device 550 can be inserted in the other direction as well. After insertion and/or as the device 550 enters the target area or procedural area in the patient's body, the joints 556A, 556B with the torsion springs (or other standard mechanisms) urge the segments 552A, 552B from their insertion position to their triangular position. As the segments 552A, 552B contact each other to form joint 558, the two segments are coupled together with mating components that semi-lock the segments 552A, 552B together. That is, the two segments 552A, 552B can only be separated at the joint 558 by a force sufficient to overcome the semi-lock. Any such known mating component or coupling component, including any mechanical or magnetic mating component(s), can be incorporated into the device 550 for this purpose.

Thus, according to one embodiment, the device 550 can be in its insertion configuration during insertion into the patient. As the device 550 enters the target cavity and exits the port or incision, the torsion springs or other mechanisms at the joints 556A, 556B cause the two segments 552A, 552B to move toward each other until they couple to form the triangular configuration. The device 550 can then be attached to the abdominal wall by some method such as an external magnetic handle. Alternatively, the device 550 can be positioned anywhere in the cavity of the patient as desired by the user. The device 550 is then used to perform some sort of procedure.

Subsequently, when the procedure is complete, the device 550 can be retracted from the cavity. To do so, the surgeon uses a grasping or retrieval tool such as a Endo Babcock grasper made by Covidien in Mansfield, Mass., to attach to or otherwise grasp the ball 584 at the joint 558 and apply sufficient force to overcome the semi-lock of the joint 558. Alternatively, any retrieval component can be positioned at the end of segment 552A or elsewhere on the device 550 for grasping or otherwise coupling to for purposes of removing the device 550 from the patient's body. When the coupling of the semi-lock is overcome, the force urges the segments 552A, 552B away from each other, thereby making it possible for the surgeon to pull the ball 584 through a port or incision and out of the patient, thereby forcing the device 550 into its insertion configuration.

The multiple segments provided in the various embodiments of the device disclosed herein result in significantly more payload space than a single cylindrical body. The increased payload space results in increased capabilities for the device in the form of more, bigger, or more complex operational components, more, bigger, or more complex motors, magnets (as described below) and other similar benefits relating to the availability of more space for more, bigger, or more complex components. For example, FIG. 28B depicts a side view of the device 550 according to one embodiment that shows the payload space available in segment 552B. More specifically, segment 552B and its coupled arm 562 have payload spaces 586, 588, 590, 592, 594 that can be used to accommodate motors, operational components, sensors, magnets (as described below) or any other type of component that could be useful for a procedural device. Similarly, each segment 552A, 552B, 554 can have such payload spaces. In addition, the segments 552A, 552B, 554 allow for maximization of the payload space available across the segments 552A, 552B, 554 by distributing the components such as motors, operational components, or magnets to maximize their effectiveness while minimizing the amount of space required by each such component. For example, it might maximize effectiveness of the device 550 while minimizing the utilized space to have one large motor in one segment that provides force for operation of components in more than one segment.

It is understood that various embodiments of the segmented devices disclosed herein are in vivo devices that can be inserted into and positioned within a patient's body to perform a procedure. In one embodiment, an external controller is also provided that transmits signals to the device 550 to control the device 550 and receives signals from the device 550. In one embodiment, the controller communicates with the device 550 wirelessly. Alternatively, the controller and the device 550 are coupled via a flexible communication component such as a cord or wire (also referred to as a "tether") that extends between the device 550 and the controller.

Figure 31:
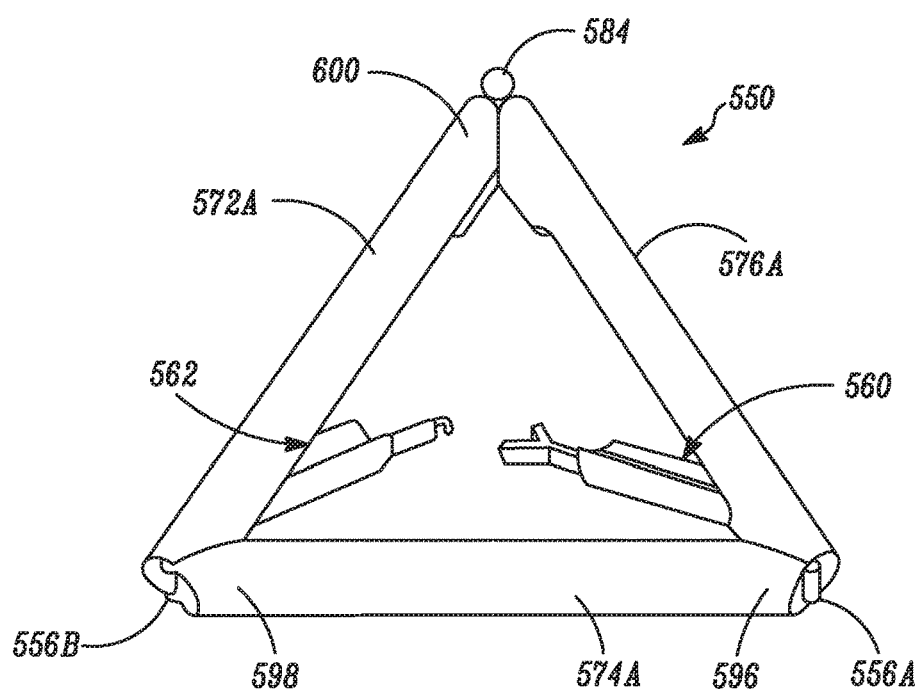
FIG. 31 is a top view of the device of FIG. 27A.

It is also understood that various embodiments of the devices disclosed herein can be used in conjunction with known attachment components to attach or otherwise position the device near, against, or adjacent to an interior cavity wall inside the patient. In one embodiment, the attachment components are one or more magnets, disposed within the device, that communicate magnetically with one or more magnets positioned outside the patient's body. The device magnets can be positioned on or in the device in any suitable configuration. For example, the device magnets in one embodiment can be positioned within the segments 552A, 552B, 554 at positions 596, 598, 600 as shown in FIG. 31. It is understood that the external magnets can be used outside the body to position and/or move the device 550 inside the body.

Figure 32:
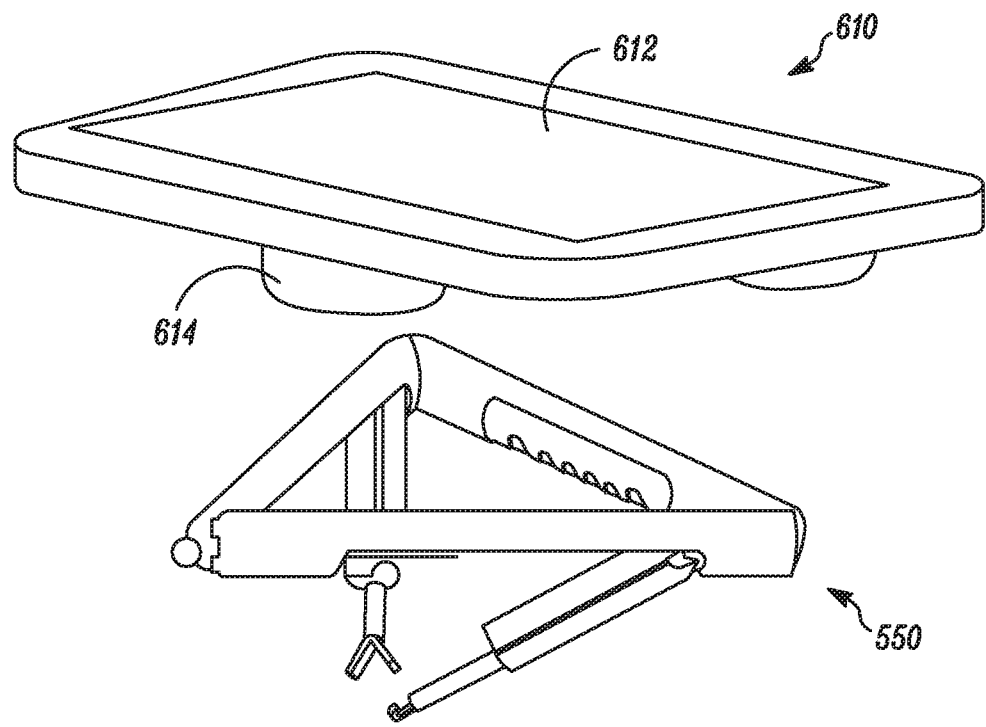
FIG. 32 is a perspective view of modular medical device control and visualization system, according to one embodiment.

It is further understood that various embodiments of the devices disclosed herein can be used in conjunction with known visualization and control components, such as the console 610 depicted in FIG. 32. The console 610 has a display 612 and magnets 614 and is positioned outside the patient such that the magnets 614 can be in magnetic communication with the device magnets (not shown) disposed within or otherwise coupled with the device 550. The console 610 can be used to move the device 550 by moving the console 610 outside the body such that the device 550 is urged to move inside the body, because the console magnets 550 are magnetically coupled with the device magnets (not shown) within the device 550 such that the device 550 remains substantially fixed in relation to the console 610. In addition, it is understood that the triangular (and quadrangular) devices disclosed and described in relation to FIGS. 27A-33 can be used in conjunction with any of the external controller or visualization components and systems disclosed and discussed above and in the applications incorporated above.

The segmented device 550, according to one embodiment, provides greater stability and operability for the device 550 in comparison to other in vivo devices. That is, a device having more than one segment such as device 550 provides for a configuration with a larger "footprint" for the device 550, thereby resulting in greater stability and leverage during use of the device 550. For example, the device 550 with the triangular configuration in FIG. 32 that is urged against the interior cavity wall of the patient by the console magnets 614 has greater stability and leverage in comparison to a device that has a smaller "footprint." That is, the device 550 can have at least three magnets (not shown) disposed at the three corners of the triangular configuration such that when the device 550 is magnetically positioned against the interior cavity wall, the arms of the device 550 can apply greater force to the target tissues while maintaining the position of the device 550 than a corresponding single cylindrical device body.

Figure 33:
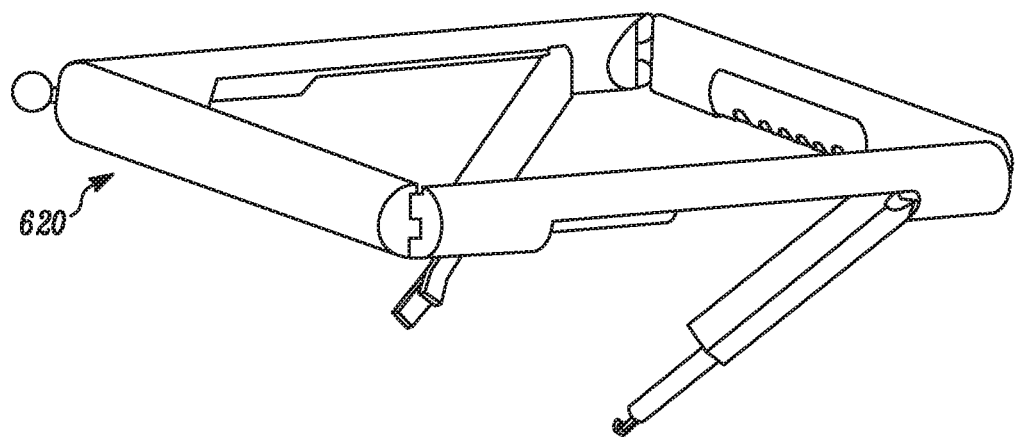
FIG. 33 is a perspective view of a modular medical device, according to one embodiment.

It is understood that the device embodiments disclosed herein are not limited to a triangular configuration. FIG. 33 depicts a device 620 having a quadrangular configuration with four segments. Similarly, devices are contemplated herein having any number of segments ranging from two segments to any number of segments that can be used for a device that can be positioned inside a patient's body. For example, a device incorporating the components and structures disclosed herein could have six or eight segments or more.

In accordance with one embodiment, the various medical devices disclosed herein and in the applications incorporated above can be used cooperatively. That is, two or more devices can be used at the same time during the same procedure to accomplish more or perform the procedure more quickly than when only one device is used at a time. As such, multiple robots (more than one device and up to any number capable of being inserted into a patient's cavity and present in the cavity at the same time for performing one or more procedures) are inserted into the patient's cavity and each controlled by the surgical team.

Figure 34:
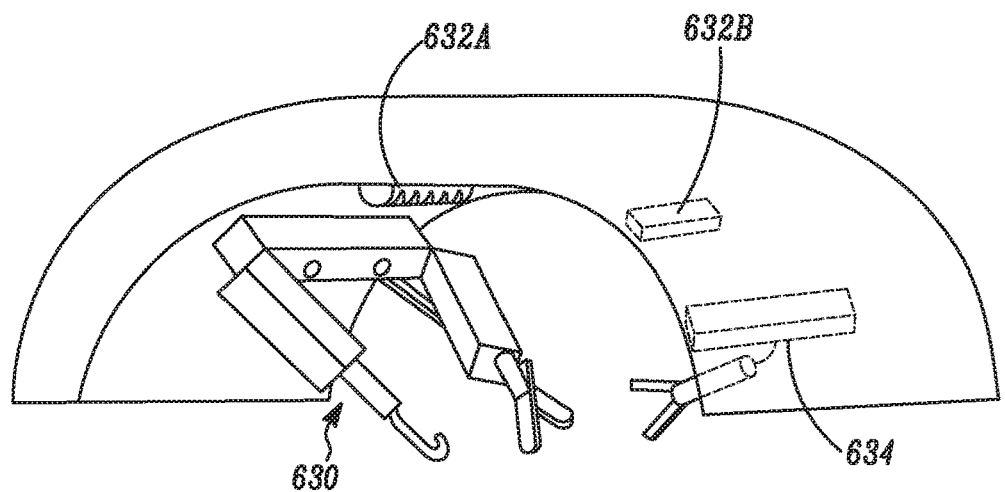
FIG. 34 is a perspective cutaway view of various medical devices operating cooperatively in a body cavity, according to one embodiment.
Figure 35:
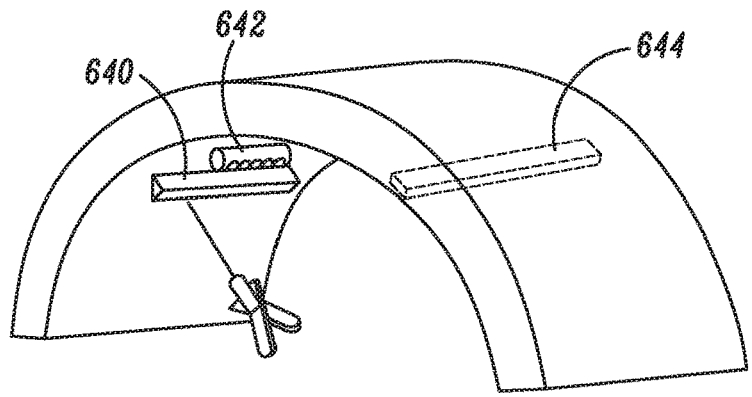
FIG. 35 is a perspective cutaway view of various medical devices operating cooperatively in a body cavity, according to another embodiment.
Figure 36:
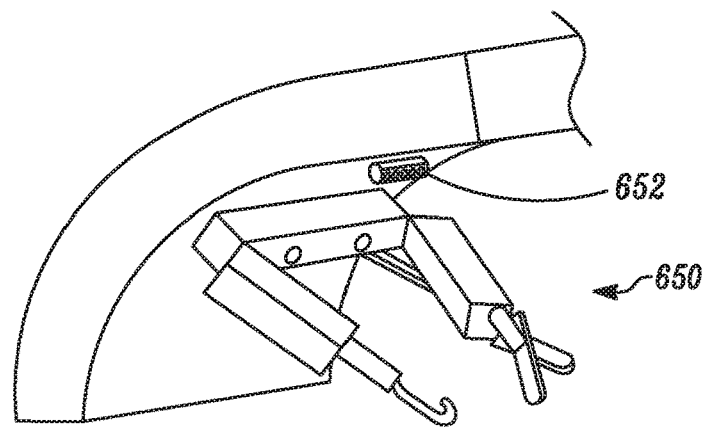
FIG. 36 is a perspective cutaway view of various medical devices operating cooperatively in a body cavity, according to a further embodiment.

FIGS. 34-36 depict three different embodiments of cooperative use of two or more medical devices together. In FIG. 34, the devices that are positioned within a cavity of a patient include a device with operational arms 630, two lighting devices 632A, 632B, and a cylindrical device having a winch component with an end effector 634. These devices can be operated at the same time using one or more external controllers and/or visualization components according to the various embodiments disclosed above or in the applications incorporated above.

Similarly, FIG. 35 depicts a cooperative procedure implementation using a cylindrical device having a winch component with an end effector 640, a lighting device 642, and a cylindrical device 644. The cylindrical device 644 can have an imaging component and/or additional operational components such as sensors, etc.

Another embodiment is depicted in FIG. 36, in which a cooperative procedure is performed using a device with arms 650 and a lighting device 652.

According to one embodiment, the devices are assembled while being introduced through a natural orifice, a port, or an incision. For instance, if insertion is through the esophagus, each robot is inserted down the overtube, which provides an "in line" ability for consistent assembly as each robot is "pushed" down the overtube. Alternatively, after insertion into the abdominal cavity, a camera and tool can be inserted to assist with the mechanical connections, or other robotic devices can be used to help with the mechanical connections.

The level of cooperation amongst two or more in vivo medical devices varies between high network communications, planning, and some autonomy, to lower level mechanical connections and surgeon control. That is, in certain embodiments, the cooperative devices can communicate with each other and perform with some level of autonomy (without input or with limited input from the user or surgeon). In an alternative implementation, the cooperative devices can simply be positioned in the same general procedural space and separately controlled by one or more users to work cooperatively to perform a procedure or procedures.

In one embodiment, two or more devices positioned in a body cavity can be coupled to each other in some fashion. It is understood that the coupling does not necessarily result in a rigid coupling of the devices to each other in all degrees. As such, the configuration(s) of two or more devices may adapt to the varying geometry of each patient, disturbances to the abdominal wall, and respiration cycle. According to one implementation, one benefit of coupling the devices is to maintain a set distance between the devices for vision, lighting, tissue manipulation, and other procedural purposes.

Although the present invention has been described with reference to preferred embodiments, persons skilled in the art will recognize that changes may be made in form and detail without departing from the spirit and scope of the invention.

What is claimed is:

1. A robotic device, comprising:
   (a) an elongate device body constructed and arranged to be positionable within a cavity of a patient;
   (b) a connection component operably coupled with the elongate device body;
   (c) a first operational arm comprising:
      (i) a first inner arm segment operably coupled with the device body via a first shoulder joint at a first end of the elongate device body;
      (ii) a first outer arm segment operably coupled with the first inner arm segment via a first elbow joint; and
      (iii) a first procedural tool operably coupled with the first outer arm segment;
   (e) a second operational arm comprising:
      (i) a second inner arm segment operably coupled with the device body via a second shoulder joint at a second end of the elongate device body;
      (ii) a second outer arm segment operably coupled with the second inner arm segment via a second elbow joint; and
      (iii) a second procedural tool operably coupled with the second outer arm segment; and
   (f) at least one actuator disposed within each arm, the at least one actuator being configured to actuate movement of the arm, wherein the at least one actuator is operably coupled to a physical linkage extending to an external component.

2. The robotic device of claim 1, wherein each of the first and second operational arms has at least four degrees of freedom.

3. The robotic device of claim 1, further comprising:
   (a) at least one imaging component operably coupled to the device body; and
   (b) an external controller operably coupled to the device body, the external controller comprising:
      (i) an image display component operably coupled to the at least one imaging component, the image display component configured to display images acquired by the at least one imaging component; and
      (ii) at least one joystick operably coupled to at least one of the first and second operational arms, the at least one joystick configured to control the at least one of the first and second operational arms via the physical linkage.

4. The robotic device of claim 1, wherein each of the first and second operational arms has at least three degrees of freedom.

5. The robotic device of claim 1, wherein the first and second procedural tools are each chosen from a group consisting of a scalpel, a biopsy tool, a cauterizer, a forceps, a dissector, clippers, a stapler, and an ultrasound probe.

6. The robotic device of claim 1, wherein the connection component is a tether.

7. The robotic device of claim 1, wherein the external component is an external power source operably coupled to the physical linkage.

8. The robotic device of claim 1, further comprising at least one imaging component operably coupled with the device body, wherein the at least one imaging component is disposed between the first and second operational arms such that the first and second operational arms are viewable by a user via the at least one imaging component during operation of the first and second operational arms.

9. The robotic device of claim 8, further comprising an external controller operably coupled to the first and second operational arms and the at least one imaging component.

10. The robotic device of claim 9, wherein the external controller comprises:
   (a) an image display component operably coupled to the at least one imaging component, the image display component configured to display images acquired by the at least one imaging component; and
   (b) at least one joystick operably coupled to at least one of the first and second operational arms, the at least one joystick configured to control the at least one of the first and second operational arms.

11. A robotic device, comprising:
   (a) an elongate device body constructed and arranged to be positionable within a cavity of a patient, the elongate device body comprising a first shoulder joint at a first end and a second shoulder joint at a second end opposite the first end;
   (b) a connection component operably coupled with the elongate device body;
   (c) a first operational arm comprising:
      (i) a first inner arm segment operably coupled with the device body via the first shoulder joint;
      (ii) a first outer arm segment operably coupled with the first inner arm segment via a first elbow joint; and
      (iii) a first procedural tool operably coupled with the first outer arm segment;
   (d) a second operational arm comprising:
      (i) a second inner arm segment operably coupled with the device body via the second shoulder joint;
      (ii) a second outer arm segment operably coupled with the second inner arm segment via a second elbow joint; and
      (iii) a second procedural tool operably coupled with the second outer arm segment;

(f) at least one actuator disposed within each arm, the at least one actuator being configured to actuate movement of the arm, wherein the at least one actuator is operably coupled to a physical linkage extending to an external component; and (g) at least one imaging component operably coupled with the device body.

12. The robotic device of claim 11, wherein each of the first and second operational arms has at least three degrees of freedom.

13. The robotic device of claim 11, wherein each of the first and second operational arms has at least four degrees of freedom.

14. The robotic device of claim 11, further comprising an external controller operably coupled to the at least one imaging component and the first and second operational arms, the external controller comprising:

(a) an image display component operably coupled to the at least one imaging component, the image display component configured to display images acquired by the at least one imaging component; and (b) at least one joystick operably coupled to at least one of the first and second operational arms, the at least one joystick configured to control at least one of the first and second operational arms.

15. The robotic device of claim 11, wherein the first and second procedural tools are each chosen from a group consisting of a scalpel, a biopsy tool, a cauterizer, a forceps, a dissector, clippers, a stapler, and an ultrasound probe.

16. A method of surgery comprising:

making an incision in a patient, wherein the incision provides access to a target cavity in the patient;

inserting a robotic device through the incision and into the target cavity in the patient, the robotic device comprising:

(a) an elongate device body;

(b) a connection component operably coupled with the device body;

(c) a first operational arm comprising:
  (i) a first inner arm segment operably coupled with the device body via a first shoulder joint at a first end of the elongate device body;
  (ii) a first outer arm segment operably coupled with the first inner arm segment via a first elbow joint; and
  (iii) a first operational component operably coupled with the first outer arm segment;

(e) a second operational arm comprising:
  (i) a second inner arm segment operably coupled with the device body via a second shoulder joint at a second end of the elongate device body;
  (ii) a second outer arm segment operably coupled with the second inner arm segment via a second elbow joint; and
  (iii) a second operational component operably coupled with the second outer arm segment; and (f) at least one actuator disposed within each arm, the at least one actuator being configured to actuate movement of the arm, wherein the at least one actuator is operably coupled to a physical linkage extending to an external component; and performing a procedure in the target cavity of the patient using at least the robotic device.

17. The method of claim 16, wherein making the incision in the patient comprises making no more than two incisions in the patient.

18. The method of claim 16, wherein performing the procedure further comprises performing the procedure using the robotic device and at least one additional device.

19. The method of claim 16, wherein the external component is an external controller comprising an external power source operably coupled to the at least one actuator, wherein performing the procedure further comprises operating the external controller, wherein the external power source is configured to transmit force to the at least one actuator via the physical linkage for actuating movement of the arms.

20. The robotic device of claim 7, wherein the physical linkage is an actuation system.

* * * * *